US008956839B2

(12) United States Patent
Rambo et al.

(10) Patent No.: US 8,956,839 B2
(45) Date of Patent: Feb. 17, 2015

(54) THIOL-ENE COUPLING CHEMISTRY FOR IMMOBILIZATION OF BIOCATALYSTS

(71) Applicant: Akermin, Inc., St. Louis, MO (US)

(72) Inventors: Brett M. Rambo, St. Charles, MO (US); John Reardon, Lake St. Louis, MO (US); Aleksey Zaks, Hoboken, NJ (US)

(73) Assignee: Akermin, Inc., St. Louis, MO (US)

( * ) Notice: Subject to any disclaimer, the term of this patent is extended or adjusted under 35 U.S.C. 154(b) by 0 days.

(21) Appl. No.: 13/911,275

(22) Filed: Jun. 6, 2013

(65) Prior Publication Data

US 2013/0330801 A1   Dec. 12, 2013

Related U.S. Application Data

(60) Provisional application No. 61/656,760, filed on Jun. 7, 2012.

(51) Int. Cl.
*C12N 11/14*   (2006.01)

(52) U.S. Cl.
CPC ..... *C12N 11/14* (2013.01); *Y02C 10/04* (2013.01)
USPC .......................................... 435/176

(58) Field of Classification Search
None
See application file for complete search history.

(56) References Cited

U.S. PATENT DOCUMENTS

| | | | |
|---|---|---|---|
| 6,524,843 | B1 | 2/2003 | Blais et al. |
| 7,176,017 | B2 | 2/2007 | Parent et al. |
| 7,579,185 | B2 | 8/2009 | Parent et al. |
| 7,596,952 | B2 | 10/2009 | Fradette et al. |
| 7,820,432 | B2 | 10/2010 | Parent et al. |
| 7,998,714 | B2 | 8/2011 | Gellett et al. |
| 8,066,965 | B2 | 11/2011 | Fradette et al. |
| 8,178,332 | B2 | 5/2012 | Gellett et al. |
| 8,277,769 | B2 | 10/2012 | Fradette et al. |
| 8,329,458 | B2 | 12/2012 | Parent et al. |
| 8,329,459 | B2 | 12/2012 | Parent et al. |
| 8,329,460 | B2 | 12/2012 | Parent et al. |
| 8,435,479 | B2 | 5/2013 | Fradette et al. |
| 8,480,796 | B2 | 7/2013 | Fradette et al. |
| 8,722,391 | B2 | 5/2014 | Fradette et al. |
| 2006/0127971 | A1 | 6/2006 | Giordano et al. |
| 2007/0006774 | A1 | 1/2007 | Rogers et al. |
| 2008/0241877 | A1 | 10/2008 | Ying et al. |
| 2009/0170180 | A1 | 7/2009 | Bond et al. |
| 2010/0086983 | A1* | 4/2010 | Gellett et al. ............... 435/168 |
| 2011/0300623 | A1 | 12/2011 | Gellett et al. |
| 2012/0122195 | A1 | 5/2012 | Fradette et al. |
| 2012/0220025 | A1 | 8/2012 | Gellett et al. |
| 2013/0267004 | A1 | 10/2013 | Rambo et al. |
| 2013/0273609 | A1* | 10/2013 | Ngo et al. ................. 435/91.2 |

FOREIGN PATENT DOCUMENTS

| | | |
|---|---|---|
| WO | 00/10691 A1 | 3/2000 |
| WO | 2011/060129 A1 | 5/2011 |
| WO | WO 2012122404 A2 * | 9/2012 |

OTHER PUBLICATIONS

Arazawa, D.T., Oh, H.-I., Ye, S.-H., Johnson Jr., C.A., Woolley, J.R., Wagner, W.R., and Federspeil, W.J. "Immobilized Carbonic Anhydrase on Hollow Fiber Membranes Accelerates CO2 Removal from Blood", Journal of Membrane Science, EPub Feb. 2013, vol. 403-404, pp. 25-31.*
Chen, Y., et al., "Vinyl Functionalized Silica Hybrid Monolith-Based Trypsin Microreactor for On Line Digestion and Separation via Thiol-ene "Click" Strategy," Journal of Chromatography A, 2011, pp. 7982-7988, vol. 1218.
Drevon, G. F., et al., "Enzyme-Containing Michael-Adduct-Based Coatings," Biomacromolecules, 2003, pp. 675-682, vol. 4, No. 3.
Hoyle, C. E., et al., "Thiol-Ene Click Chemistry," Angewandte Chemie Int. Ed., 2010, pp. 1540-1573, vol. 49.
Hvilsted, S., "Facile Design of Biomaterials by 'Click' Chemistry," Polymer International, 2012, 10 Pages.
Jonkheijm, P., et al., "Photochemical Surface Patterning by the Thiol-Ene Reaction," Angewandte Chemie Int. Ed., 2008, pp. 4421-4424, vol. 47.
Killops, K. L., et al., "Robust, Efficient, and Orthogonal Synthesis of Dendrimers via Thiol-ene "Click" Chemistry," Journal of the American Chemical Society, 2008, pp. 5062-5064, vol. 130, No. 15.
Kohn, M., et al., "Functional Evaluation of Carbohydrate-Centred Glycoclusters by Enzyme-Linked Lectin Assay: Ligands for Concanavalin A," ChemBioChem: A European Journal of Chemical Biology, Jun. 2004, pp. 771-777, vol. 5, No. 6.
Kumari, S., et al., "Functionalization of SBA-15 Mesoporous Materials Using "Thiol-Ene Click" Michael Addition Reaction," The Journal of Physical Chemistry C, 2011, pp. 17774-17781, vol. 115.
Wittrock, S., et al., "Synthetic Vaccines of Tumor-Associated Glycopeptide Antigens by Immune-Compatible Thioether Linkage to Bovine Serum Albumin," Angewandte Chemie Int. Ed., 2007, pp. 5226-5230, vol. 46, No. 27.
Zou, J., et al., "Clicking Well-Defined Biodegradable Nanoparticles and Nanocapsules by UV-Induced Thiol-Ene Cross-Linking in Transparent Miniemulsions," Advanced Materials, 2011, pp. 4274-4277, vol. 23.
Alper, E., "Comments on the Effect of Carbonic Anhydrase on Carbon Dioxide Absorption," Chemical Engineering Science, Shorter Communications, 1978, pp. 1399-1400, vol. 33.
Alper, E., et al., "Comments on 'Gas Absorption with Catalytic Reaction'," Chemical Engineering Science, Shorter Communications, 1981, pp. 1097-1099, vol. 36.

(Continued)

*Primary Examiner* — Allison Fox
*Assistant Examiner* — Michelle F Paguio Frising
(74) *Attorney, Agent, or Firm* — Senniger Powers LLP

(57) ABSTRACT

The present invention generally relates to immobilized biocatalysts or immobilized enzymes for use in carbon capture and sequestration technology. Thiol-ene chemistry is used to couple a biocatalyst, particularly carbonic anhydrase, to a substrate including a substrate, a solid support, a microparticle, a nanoparticle, or a combination thereof.

21 Claims, 13 Drawing Sheets

(56) References Cited

OTHER PUBLICATIONS

Alper, E., et al., "Gas Absorption Mechanism in Catalytic Slurry Reactors," Chemical Engineering Science, 1980, pp. 217-222, vol. 35.

Alper, E., et al., "On the Mechanism of Enzyme-Catalysed Gas-Liquid Reactions: Absorption of CO2 Into Buffer Solutions Containing Carbonic Anhydrase," Chemical Engineering Science, 1980, pp. 2147-2156, vol. 35.

Crumbliss, A. L., et al., "Preparation and Activity of Carbonic Anhydrase Immobilized on Porous Silica Beads and Graphite Rods," Biotechnology and Bioengineering, 1988, pp. 796-801, vol. 31, No. 8.

\* cited by examiner

THIOL-ENE COUPLING CHEMISTRY FOR IMMOBILIZATION OF BIOCATALYSTS

CROSS-REFERENCE TO RELATED APPLICATIONS

This application is a Non-Provisional Patent Application of U.S. Provisional Patent Application Ser. No. 61/656,760, filed Jun. 7, 2012, the entirety of which is herein incorporated by reference.

FIELD OF THE INVENTION

The present invention generally relates to the immobilization of biocatalysts using thiol-ene chemistry. The biocatalyst can be immobilized to a range of substrates including a solid support, a microparticle, a nanoparticle, or a combination thereof. The immobilized biocatalyst can be an enzyme that reacts with carbon dioxide, such as carbonic anhydrase. Furthermore, the immobilized biocatalyst can be utilized for carbon capture or carbon separation technology.

BACKGROUND OF THE INVENTION

Technologies are being developed for capturing carbon dioxide ($CO_2$) from industrial gas streams to reduce energy costs and the environmental impact of $CO_2$ in the atmosphere. Major sources of $CO_2$ emissions include power plants, cement kilns, natural gas processing facilities, ammonia plants, and hydrogen plants. The captured $CO_2$ can be sequestered or can be reutilized for: enhanced oil recovery, food processing or accelerated algae growth that could have multiple applications. In the cases of natural gas processing and ammonia production, removal of $CO_2$ is a necessary step to meet product specifications. In the case of industrial hydrogen production, $CO_2$ removal can improve plant efficiency and increase product output.

Currently several alternate $CO_2$ capture technologies are in various stages of commercial practice and development. These include chemical absorption using amine solvents (particularly monoethanolamine—MEA), physical adsorption, membrane separation, and cryogenic distillation. In addition, technologies such as oxycombustion and Integrated Gasification Combined Cycle, which remove the $CO_2$ and other impurities to produce a compressed hydrogen gas stream that can be combusted in a gas turbine, are being considered as more cost-effective and environmentally friendly approach to generate electric power using coal. Chemical absorption with amines is currently the lowest cost method of $CO_2$ removal for the majority of gas streams. MEA systems are more reactive, and therefore preferred, but the energy requirements to remove the absorbed $CO_2$ from the MEA is very high, at about 4 million BTU/tonne of $CO_2$ and can require up to about one-third of a power plant's boiler output. One emerging alternative to primary and secondary amine stripping is to incorporate biocatalysts that are specific for carbon dioxide conversion ($CO_2$) in the presence of low duty solvents, subsequently lowering the regeneration energy requirements and lowering overall cost. Carbonic anhydrases (CAs), EC 4.2.1.1, are a family of enzymes that are ubiquitous in nature and are known to catalyze a reversible conversion of bicarbonate into $CO_2$ and water.

There is a need in the art for advanced materials, compositions, methods, processes, and systems which improve the stability and efficiency of enzymes for use in the catalysis of industrial processes in general and carbon capture in particular.

SUMMARY OF THE INVENTION

One aspect of the invention is a biocatalyst immobilized using a linking group to attach to a substrate. The substrate can be a solid support such as a ceramic or silicate surface, microparticle, or nanoparticle. The biocatalyst can be an enzyme that hydrates carbon dioxide, such as carbonic anhydrase.

Another aspect is an immobilized biocatalyst comprising a substrate; and a biocatalyst linked to the substrate through a linking moiety. The linking moiety comprises a $C_1$ to $C_{30}$ alkylene wherein at least one of the —$CH_2$— groups of the alkylene group is replaced by —S—; and optionally, each of one or more of the other —$CH_2$— groups of the alkylene group is independently replaced by —($CH_2$—$CH_2$—O)$_x$—, —O—, —C(O)—, —NR—, —Si(OR$_1$)(OR$_2$)—, —Si(R$_5$)(OR$_2$)—, —Si(Cl)(Cl)—, arylene, cycloalkylene, heteroarylene, or heterocyclo; or optionally, each of one or more of the other —$CH_2$— groups of the alkylene group is independently substituted with a —OH, —NR$_3$R$_4$, or —C(O)OH, wherein x is an integer from 4 to 2300, R$_1$ and R$_2$ are independently hydrogen, alkyl, or another silicon atom attached to the substrate through an —O— group, R$_3$ and R$_4$ are independently hydrogen, alkyl, or —CHO, and R$_5$ is alkyl; wherein the biocatalyst catalyzes hydration of carbon dioxide.

Yet another aspect is an immobilized biocatalyst comprising a substrate having a thiol group attached to its surface, a biocatalyst having an attached alkene group, and a linking moiety between the substrate and the biocatalyst. The linking group between the substrate and the biocatalyst being derived from reaction of the thiol group attached to the substrate surface and the alkene group attached to the biocatalyst and the biocatalyst catalyzes hydration of carbon dioxide.

A further aspect is an immobilized enzyme comprising a substrate having a thiol group attached to its surface, an enzyme having an attached alkene group, and a linking moiety between the substrate and the enzyme. The linking group between the substrate and the enzyme being derived from reaction of the thiol group attached to the substrate surface and the alkene group attached to the enzyme.

Another aspect is a method of preparing an immobilized biocatalyst comprising functionalizing a substrate with a thiol group; functionalizing a biocatalyst for hydrating carbon dioxide with an alkene group; and reacting the thiol group of the substrate with the alkene group of the biocatalyst to form a moiety linking the substrate to the biocatalyst.

Yet another aspect is an immobilized carbonic anhydrase comprising a substrate having an alkene group attached to its surface, a carbonic anhydrase having an attached thiol group, and a linking moiety between the substrate and the biocatalyst. The linking group between the substrate and the biocatalyst being derived from reaction of the thiol group attached to the carbonic anhydrase and the alkene group attached to the substrate.

A further aspect is an immobilized enzyme comprising a substrate having an alkene group attached to its surface, an enzyme having an attached thiol group, and a linking moiety between the substrate and the enzyme. The linking group between the substrate and the enzyme being derived from reaction of the alkene group attached to the substrate surface and the thiol group attached to the enzyme.

DESCRIPTION OF THE INVENTION

Figure 1:
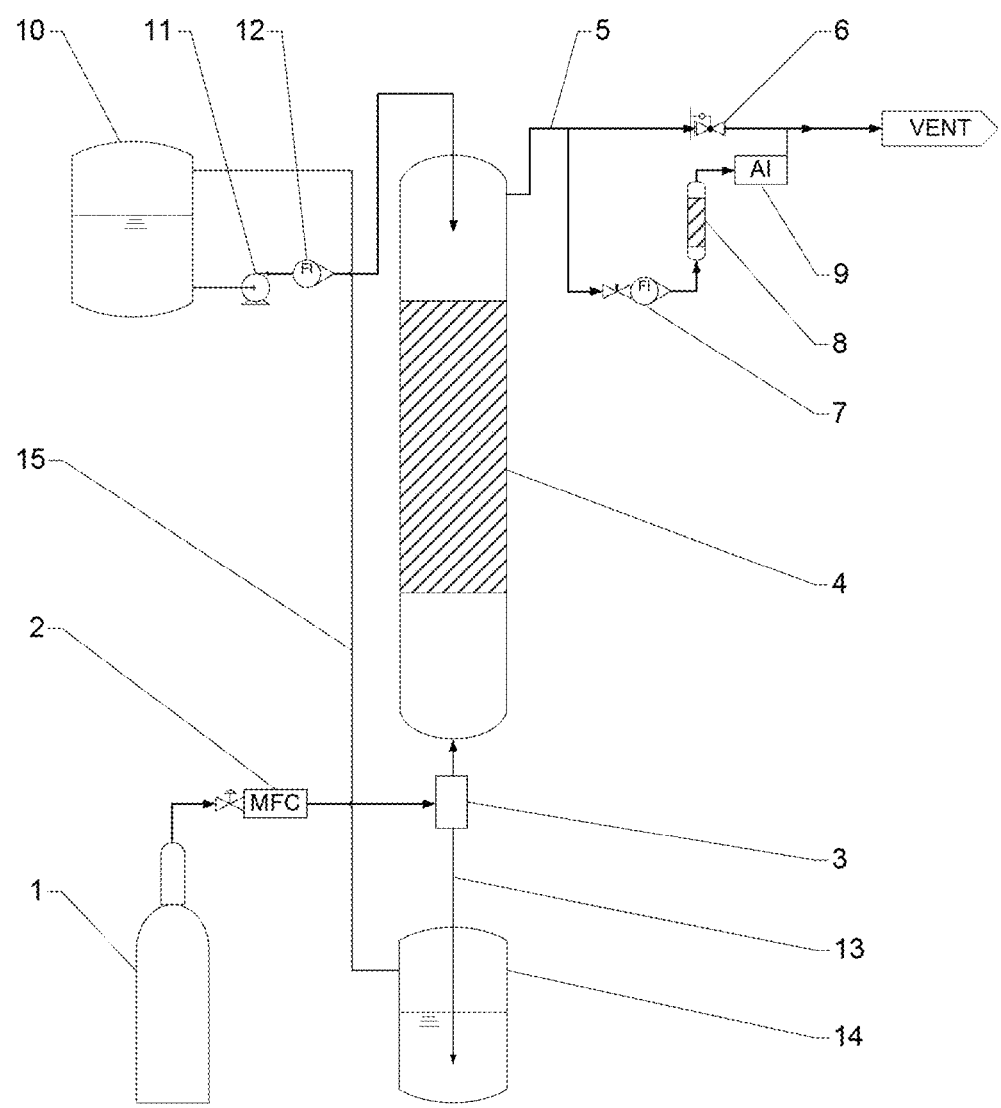
FIG. 1 is a schematic of a single-pass flow-through reactor.

The present invention is directed to immobilized biocatalysts that either catalyze the hydration of carbon dioxide and/or are immobilized carbonic anhydrases and their use in carbon capture and sequestration technology. It has been discovered that thiol-ene chemistry is an effective method for immobilizing biocatalysts on functionalized substrates, including solid supports, microparticles, nanoparticles, and combinations thereof. This chemistry provides many advantages including its chemoselectivity, tolerance to a wide variety of functional groups, usefulness in aqueous solvents, lack of pH sensitivity, and lack of oxygen sensitivity. The resulting immobilized biocatalysts, particularly carbonic anhydrase, retain their activity and provide a particularly efficient immobilization of carbonic anhydrase.

Immobilized Biocatalysts

The immobilized biocatalyst comprises a substrate and a biocatalyst linked to the substrate through a linking moiety. The linking moiety can comprise a $C_1$ to $C_{30}$ alkylene wherein at least one of the —$CH_2$— groups of the alkylene group is replaced by —S—; and optionally, each of one or more of the other —$CH_2$— groups of the alkylene group is independently replaced by —($CH_2$—$CH_2$—O)$_x$—, —O—, —C(O)—, —$NR_3$—, —Si(OR$_1$)(OR$_2$)—, —Si(R$_5$)(OR$_2$)—, —Si(Cl)(Cl)—, arylene, cycloalkylene, heteroarylene, or heterocyclo; or optionally, each of one or more of the other —$CH_2$— groups of the alkylene group is independently substituted with a —OH, —$NR_3R_4$, or —C(O)OH, wherein x is an integer from 4 to 2300, $R_1$ and $R_2$ are independently hydrogen, alkyl, or another silicon atom attached to the substrate through an —O— group, $R_3$ and $R_4$ are independently hydrogen, alkyl, or —CHO, and $R_5$ is alkyl. The biocatalyst catalyzes hydration of carbon dioxide.

The linking moiety of the immobilized biocatalyst can also comprise a $C_1$ to $C_{20}$ alkylene wherein at least one of the —$CH_2$— groups of the alkylene group is replaced by —S—, and optionally, each of one or more of the other —$CH_2$— groups of the alkylene group is independently replaced by —($CH_2$—$CH_2$—O)$_x$—, —O—, —C(O)—, —$NR_3$—, or —Si(OR$_1$)(OR$_2$)—, and each of one or more of the other —$CH_2$— groups of the alkylene group is independently substituted with a —OH, or —C(O)OH, wherein x is an integer from 4 to 2300, $R_1$ and $R_2$ are independently hydrogen, methyl, or another silicon atom attached to the substrate through an —O— group, and $R_3$ is hydrogen.

The linking moiety of the immobilized biocatalyst can also comprise a $C_1$ to $C_{20}$ alkylene wherein at least one of the —$CH_2$— groups of the alkylene group is replaced by —S—, and each of one or more of the other —$CH_2$— groups of the alkylene group is independently replaced by —($CH_2$—$CH_2$—O)$_x$—, —O—, —C(O)—, —$NR_3$—, or —Si(OR$_1$)(OR$_2$)—, and each of one or more of the other —$CH_2$— groups of the alkylene group is independently substituted with a —C(O)OH, wherein x is an integer from 4 to 2300, $R_1$ and $R_2$ are independently hydrogen, methyl, or another silicon atom attached to the substrate through an —O— group, and $R_3$ is hydrogen.

When a —$CH_2$— group is replaced by a —S—, a thioether moiety is formed when the —S— is attached to two other —$CH_2$— groups. Also, when a —$CH_2$— group is replaced by a —O— group, an ether moiety is formed when —O— is attached to two other —$CH_2$— groups. When a —$CH_2$— group is replaced by a —$NR_3$— group, an amine moiety is formed. When a —$CH_2$— group is replaced by a —C(O)— group, a keto moiety is formed. Further, when a —O— group replaces a —$CH_2$— adjacent to a —$CH_2$— replaced by a —C(O)— group, an ether moiety is formed. Also, when a —$NR_3$— group replaces a —$CH_2$— adjacent to a —$CH_2$— group replaced by a —C(O)— group, an amide moiety is formed. Additionally, when a —$CH_2$— group is replaced by a —($CH_2$—$CH_2$—O)$_x$—, only one —$CH_2$— group is replaced by the polymeric group.

Further, when a —$CH_2$— group is replaced by a —Si(OR$_1$)(OR$_2$)—, —Si(R$_5$)(OR$_2$)—, or a-Si(Cl)(Cl)—, the carbon atom of the —$CH_2$— group is replaced by a silicon atom with its attached groups. Further, when $R_1$ or $R_2$ is another silicon atom attached to the substrate through an —O— group, the —O— group attached to the $R_1$ or $R_2$ group can be attached to the surface of the substrate and the $R_1$ or $R_2$ group is then the silicon atom in the vicinity of that —O— that is attached to the substrate through a different —O— group.

When the linking groups are described as replacing the —$CH_2$— group or as a substituent of the —$CH_2$— group, the groups that can replace the —$CH_2$— group or be a substituent on the —$CH_2$— group can replace any —$CH_2$— group in the chain or be a substituent on any remaining —$CH_2$— group. Further, the groups that replace the —$CH_2$— groups can replace adjacent —$CH_2$— groups and each group independently can be used to replace one or more —$CH_2$— groups. Also, the groups that are substituents on the —$CH_2$— groups can be substituents on adjacent —$CH_2$— groups and each group independently can be a substituent on one or more —$CH_2$— groups.

The immobilized biocatalyst can also comprise a substrate having a thiol group attached to its surface, a biocatalyst having an attached alkene group, and a linking moiety between the substrate and the biocatalyst, the linking group between the substrate and the biocatalyst being derived from reaction of the thiol group attached to the substrate surface and the alkene group attached to the biocatalyst. The biocatalyst catalyzes hydration of carbon dioxide.

The thiol linking group of the immobilized biocatalyst is attached to the surface of the substrate through an —O— by a thiol linking group that comprises a $C_1$ to $C_{10}$ alkylene group; or a $C_1$ to $C_{10}$ alkylene group wherein each of one or more of the —$CH_2$— groups of the alkylene group is independently replaced by —O—, —$Si(OR_1)(OR_2)$—, —$Si(R_5)(OR_2)$—, or —$Si(Cl)(Cl)$—; or optionally, each of one or more of the other —$CH_2$— groups of the alkylene group is independently substituted with a —OH, —C(O)OH, or —$NR_3R_4$, wherein $R_1$, and $R_2$ are independently hydrogen, alkyl, or another silicon atom attached to the substrate through an —O— group; $R_3$ and $R_4$ are independently hydrogen, alkyl, or —CHO; and $R_5$ is alkyl.

The thiol linking group of the immobilized biocatalyst can comprise a $C_1$ to $C_5$ alkylene group, or a $C_1$ to $C_6$ alkylene group wherein each of one or more of the —$CH_2$— groups of the alkylene group is independently replaced by —$Si(OR_1)(OR_2)$—, —$Si(R_5)(OR_2)$—, or —$Si(Cl)(Cl)$—; wherein $R_1$ and $R_2$ are independently hydrogen, alkyl, or another silicon atom attached to the substrate through an —O— group, and $R_5$ is alkyl.

The thiol linking group of the immobilized biocatalyst can also comprise a $C_1$ to $C_6$ alkylene group wherein one of the —$CH_2$— groups of the alkylene group is replaced by —$Si(OR_1)(OR_2)$—; wherein $R_1$ and $R_2$ are independently hydrogen, alkyl, or another silicon atom attached to the substrate through an —O— group.

The immobilized biocatalyst or immobilized enzyme can have an alkene group attached to the biocatalyst by an alkene linking group that comprises a $C_1$ to $C_{20}$ alkylene or a $C_1$ to $C_{50}$ alkylene wherein each of one or more of the —$CH_2$— groups of the alkylene group is independently replaced by —($CH_2$—$CH_2$—O)$_x$—, —O—, —C(O)—, —$NR_3$—, arylene, cycloalkylene, heteroarylene, or heterocyclo, or optionally, each of one or more of the other —$CH_2$— groups of the alkylene group is independently substituted with a —OH, —$NR_3R_4$, or —C(O)OH, wherein x is an integer from 4 to 2300, and $R_3$ and $R_4$ are independently hydrogen, alkyl, or —CHO.

The alkene linking group can comprise a $C_1$ to $C_{20}$ alkylene wherein each of one or more of the —$CH_2$— groups of the alkylene group is independently replaced by —($CH_2$—$CH_2$—O)$_x$—, —O—, —C(O)—, or —$NR_3$—, and each of one or more of the other —$CH_2$— groups of the alkylene group is independently substituted with a —OH, —C(O)OH, or —$NR_3R_4$, wherein x is an integer from 4 to 2300, and $R_3$ and $R_4$ are independently hydrogen or alkyl.

The alkene linking group can also comprise a $C_1$ to $C_{10}$ alkylene wherein each of one or more of the —$CH_2$— groups of the alkylene group is independently replaced by —($CH_2$—$CH_2$—O)$_x$—, —O—, —C(O)—, or —$NR_3$—, and one or more of the other —$CH_2$— groups of the alkylene group is substituted with a —C(O)OH, wherein x is an integer from 4 to 2300 and $R_3$ is hydrogen.

Particularly, the attached alkene group comprises a moiety, the moiety having the structure of formula 1

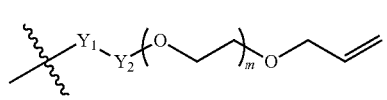

wherein m is an integer greater than 4, $Y_1$ is —$CR_{10}R_{11}$—, —O—, —S—, or —$NR_{12}$—, and $Y_2$ is —$CR_{10}R_{11}$— or —C(O)—, $R_{10}$ and $R_{11}$ are independently hydrogen, alkyl, or aryl, and $R_{12}$ is hydrogen, alkyl, or aryl.

Further, the attached alkene group comprises a moiety of Formula 1 wherein m is an integer from 4 to 2300, $Y_1$ is —$CR_{10}R_{11}$— or —$NR_{12}$—, and $Y_2$ is —$CR_{10}R_{11}$— or —C(O)—, $R_{10}$ and $R_{11}$ are hydrogen, and $R_{12}$ is hydrogen.

Also, the attached alkene group comprises a moiety of Formula 1 wherein m is an integer from 4 to 2300, $Y_1$ is —$NR_{12}$—, and $Y_2$ is —C(O)—, and $R_{12}$ is hydrogen.

For the immobilized biocatalyst, m is an integer from 4 to 115.

Further, for the immobilized biocatalyst, m is an integer from 10 to 80.

Yet further, for the immobilized biocatalyst, m is an integer from 10 to 25.

A further aspect is an immobilized enzyme comprising a substrate having a thiol group attached to its surface, an enzyme having an attached alkene group, and a linking moiety between the substrate and the enzyme. The linking group between the substrate and the enzyme being derived from reaction of the thiol group attached to the substrate surface and the alkene group attached to the enzyme.

The thiol group and alkene groups described herein above also apply to the immobilized enzyme described herein.

Biocatalyst and Enzyme

The immobilized biocatalyst also includes a structural mimic that has carbonic anhydrase activity or a biocatalyst that catalyzes hydration of carbon dioxide. Typically, the biocatalyst can be an enzyme, a ribozyme, a deoxyribozyme, an enzyme mimic, or an organic or inorganic compound that either has carbonic anhydrase activity or can catalyze hydration of carbon dioxide.

The biocatalyst that has carbonic anhydrase activity can be a carbonic anhydrase.

Further, the biocatalyst that catalyzes hydration of carbon dioxide can be a carbonic anhydrase.

The biocatalyst can also be a carbonic anhydrase that has an activity alternatively or in addition to the activity of hydrating carbon dioxide.

When the biocatalyst is an enzyme, naturally-occurring enzymes, man-made enzymes, artificial enzymes and modified naturally-occurring enzymes can be utilized. In addition, engineered enzymes that have been engineered by natural or directed evolution can be used. Stated another way, an organic or inorganic molecule that mimics an enzyme's properties can be used.

The biocatalyst that catalyzes hydration of carbon dioxide can be a carbonic anhydrase.

The biocatalyst can be a carbonic anhydrase that catalyzes hydration of carbon dioxide.

The biocatalyst can be a carbonic anhydrase that has activity other than the activity of catalyzing the hydration of carbon dioxide.

Carbonic anhydrase (CA) represents a family of structurally and genetically diverse enzymes that arose independently from different precursors as a result of convergent evolution (Tripp, B. C., Smith, K., and Ferry, J. G., Carbonic Anhydrase: New Insights for an Ancient Enzyme, *Journal of Biological Chemistry*, 2001, 276 (52), 48615-48618), (Elluche, S. and Pöggeler, S., Carbonic Anhydrases in Fungi, *Microbiology*, 2010, 156, 23-29). The various CA enzymes have been organized into five unrelated structural classes (e.g., alpha, beta, gamma, delta, and epsilon) which share no DNA sequence similarity and differ in protein structure and active site architecture. Despite these structural differences, the active sites of all classes of CA enzymes function with a single divalent metal cofactor which is essential for catalysis (Tripp, B. C., Smith, K., and Ferry, J. G., Carbonic Anhydrase: New Insights for an Ancient Enzyme, *Journal of Biological Chemistry*, 2001, 276 (52), 48615-48618). The most common metal cofactor in CA enzymes is zinc.

The α-class of CA is the predominant form expressed in mammals, and is the best characterized of all the CA classes. There are at least 16 α-CA or CA-related enzymes (Supuran, C. T., Carbonic Anhydrases—An Overview, *Current Pharmaceutical Design*, 2008, 14, 603-614) found in animals, as well as 6 forms found in bacteria. The β-class of CAs are found in green plants, blue-green algae, and bacteria (Zimmerman, S. A. and Ferry, J. G., The β and γ Classes of Carbonic Anhydrases, *Current Pharmaceutical Design*, 2008, 14, 716-721) (Rowlett, R. S., Structure and Catalytic Mechanism of the β-Carbonic Anhydrases, *Biochimica et Biophysica Acta*, 2010, 1804, 362-373). The γ-class is found in bacteria and an example would be the CA from *Methanosarcina thermophila* (CAM) (Zimmerman, S. A. and Ferry, J. G., The β and γ Classes of Carbonic Anhydrases, *Current Pharmaceutical Design*, 2008, 14, 716-721). The CAM gene has been cloned into *E. coli* and is expressed as the Zn-containing form (Alber, B. E. and Ferry, J. G., Characterization of Heterologously Produced Carbonic Anhydrase from *Methanosarcina thermophila*, *Journal of Bacteriology* (June 1996), 3270-3274), but it is more active as the Fe-, Cd-, or Co-form. The δ-class can be found in the marine diatom *Thalassiosira weissflogii* (Zimmerman, S. A. and Ferry, J. G., The β and γ Classes of Carbonic Anhydrases, *Current Pharmaceutical Design*, 2008, 14, 716-721). This protein is a dimer, with a monomeric molecular weight of 27 kD. The protein will bind Zn-, but Fe- and/or Cd-predominates in vivo. Likewise, the ζ-class is also found in the marine diatom *Thalassiosira weissflogii* (Zimmerman, S. A. and Ferry, J. G., The β and γ Classes of Carbonic Anhydrases, *Current Pharmaceutical Design*, 2008, 14, 716-721). The protein is also a dimer with a molecular weight of 50-60 kD. The catalytic properties of these two classes have not been characterized.

The mammalian CA enzymes are divided into four broad subgroups depending on the tissue or cellular compartment location (e.g., cytosolic, mitochondrial, secreted, and membrane-associated). The CA II and CA IV enzymes are the most catalytically efficient of all the CAs characterized, demonstrating rates of catalysis that are near the theoretical limit for diffusion-controlled rates. CA IV demonstrates particularly high temperature stability, which is believed to result from the presence of two disulfide linkages in the enzyme.

Bovine carbonic anhydrase II or human carbonic anhydrase IV can be used. Human carbonic anhydrase IV is available from William S. Sly at St. Louis University and is described in more detail in the following references: Okuyama, T., Sato, S., Zhu, X. L., Waheed, A., and Sly, W. S., Human carbonic anhydrase IV: cDNA cloning, sequence comparison, and expression in COS cell membranes, *Proc. Natl. Acad. Sci. USA*, 1992, 89(4), 1315-1319 and Stams, T., Nair, S. K., Okuyama, T., Waheed, A., Sly, Christianson, D. W., Crystal structure of the secretory form of membrane-associated human carbonic anhydrase IV at 2.8-Å resolution, *Proc. Natl. Acad. Sci. USA*, 1996, 93, 13589-13594.

Compounds that mimic the active site of carbonic anhydrase can also be used in the invention. For example, various metal complexes have been used to mimic the carbonic anhydrase active site. For example, $[Zn_2(3,6,9,12,20,23,26,29$-octaazatricyclo$[29.3.1.1^{14,18}]$hexatriaconta-1(34),14,16,18 (36),31(35),32-hexaene$)(CO_3)]Br_2.7H_2O$ and $[Zn_2(3,6,9,12, 20,23,26,29$-octaazatricyclo$[29.3.1.1^{14,18}]$hexatriaconta-1 (34),14,16,18(36),31(35),32-hexaene$)(CO_3)]$ $Br_2.0.5CH_3COCH_3.5H_2O$ (See Qi et al., Carbon dioxide fixation by zinc(II) complexes with macrocyclic ligand, *Inorganic Chemistry Communications*, 2008, 11 (8), 929-934). Also used as a mimic for carbonic anhydrase was [tris(2-benzimidazolylmethyl)amineZn$(OH)_2]^{2+}$, [tris(2-benzimidazolyl)amine-Zn$(OH)_2](ClO_4)_2$, and [tris(hydroxy-2-benzimidazolylmethyl)amineZn(OH)]$ClO_4.1.5H_2O$ were also used to hydrate $CO_2$. (See Nakata et al., $CO_2$ Hydration by Mimic Zinc Complex for Active Site of Carbonic Anhydrase, *Chemistry Letters*, 1997, 10, 991-992 and Echizen et al., Nucleophilic reaction by carbonic anhydrase model zinc compound: characterization of intermediates for $CO_2$ hydration and phosphoester hydrolysis, *Journal of Inorganic Biochemistry*, 2004, 98 (8), 1347-1360).

The carbonic anhydrase can be a mammalian carbonic anhydrase, a plant carbonic anhydrase, or a microbial carbonic anhydrase.

The carbonic anhydrase can also be a microbial carbonic anhydrase.

The enzyme can also comprise a lipase, a glucose isomerase, a nitrilase, a glucose oxidase, a protease, a carbonic anhydrase, a pepsin, an amylase, a fungal amylase, a maltogenic amylase, a cellulase, a lactase, an esterase, a carbohydrase, a hemicellulase, a pentosanase, a xylanase, a pullulanase, a β-glucanase, an acetolactate decarboxylase, a β-glucosidase, a glutaminase, a penicillin acylase, a chloroperoxidase, an aspartic β-decarboxylase, a cyclodextrin glycosyltransferase, a subtilisin, an aminoacylase, an alcohol dehydrogenase, an amino acid oxidase, a phospholipase, a urease, a cholesterase, a desulfinase, a lignin peroxidase, a pectinase, an oxidoreductase, a dextranase, a glucosidase, a galactosidase, a glucoamylase, a maltase, a sucrase, an invertase, a naringanase, a bromelain, a ficin, a papain, a pepsin, a peptidase, a chymosin, a thermolysin, a trypsin, a triglyceridase, a pregastric esterase, a phosphatase, a phytase, an amidase, a glutaminase, a lysozyme, a catalase, a dehydrogenase, a peroxidase, a lyase, a fumarase, a histadase, an aminotransferase, a ligase, a cyclase, a racemase, a mutase, an oxidase, a reductase, a ligninase, a laccase, a chloroperoxidase, a haloperoxidase, a hydrogenase, a nitrogenase, an oxynitrilase, or a combination thereof.

Substrate

The substrate of the immobilized biocatalyst can be an inorganic material.

Further the substrate can comprise a solid support. Desirably, the solid support is inert to the reaction conditions in terms of temperature, pH, and reactivity with the reaction mixture components for the hydration of carbon dioxide.

The substrate can be a microparticle. The microparticles have a particle size between 0.1 µm and 100 µm. Preferably, the microparticles have a size between about 1 µm and about 100 µm.

The substrate can also be a nanoparticle. The nanoparticles have a particle size between 1 nm and 100 nm. Preferably, the substrate comprises a nanoparticle.

The substrate of the immobilized biocatalyst can be a ceramic, a silicate, alumina, stainless steel, titania, or a combination thereof.

Preferably, the substrate is a ceramic or a silicate.

The substrate can be a ceramic (a sheet, a ball, a monolith, etc.), a silicate (a silica gel, a column derived from a sol-gel process, a crystalline quartz), an ordered mesoporous silicate (FSM-16, MCM-41, and SBA-15), a fumed silica nanoparticle (e.g., CAB-O-SIL® EH-5, HP-60, and H-5), an aluminum surface, and stainless steel (grade 304 and 316 and ceramic coated).

Preparation of Functionalized Carbonic Anhydrases

The functionalization of a carbonic anhydrase with polyethylene glycol is accomplished in a four-step synthetic process. The desired enzyme is placed in a buffer and stirred to homogenize. Allyl-PEG succinimide of molecular weight from 500 to 100,000 Da at a desired ratio of allyl-PEG succinimide to enzyme is then added dropwise to the beaker with stirring. The reaction mixture is stirred for 2 hours and purified by dialysis in dialysis tubing using the desired molecular weight cut off (MWCO). The allyl-PEG functionalized enzyme is then lyophilized to dryness before use. The extent of functionalization can be controlled by changing the ratio of allyl-PEG succinimide to enzyme used in the above procedure. This procedure results in an enzyme that is allyl-PEG functionalized. Thus, when the enzyme that is functionalized is carbonic anhydrase, this can be referred to as allyl-PEG functionalized carbonic anhydrase (CA).

A similar procedure is used for the functionalization of an enzyme with N-acryloxysuccinimide. N-acryloxysuccinimide is dissolved in a minimal amount of methyl sulfoxide and then added dropwise to the enzyme in buffer. Alternatively, N-acryloxysuccinimide powder can be added directly to the enzyme/buffer solution. Thus, when the enzyme to be functionalized is carbonic anhydrase, this enzyme can be referred to as acryl-PEG functionalized carbonic anhydrase (CA).

The enzyme can comprise a carbonic anhydrase.

For this application, it is preferential that the functional groups are hydrophilic and that they provide sufficient spacing from the surface so that the coupled enzyme has the desired degrees of freedom. Thus, different molecular weight polyethylene glycols, polyethylene oxides, polyvinyl alcohols, and polysaccharides could be used as substitute functional linkers on the enzyme. Acrylate functionalized carbonic anhydrase can be used to prepare the immobilized biocatalyst. In our hands, this material has a reactivity such that it polymerizes with itself in the presence of radicals before reacting with the substrate surface.

Further, a thiol group can be attached to the biocatalyst or enzyme or a thiol group already present in the biocatalyst or enzyme can be used to react with the alkene group attached to the substrate. The functionalization of a biocatalyst can be made using, for example, a haloalkane thiol that could react with an amine group attached to the biocatalyst. The haloalkane thiol can be a chloroalkane thiol. The chloroalkane thiol can be chloroethane thiol, chloropropane thiol, chlorobutane thiol, chloropentane thiol, chlorohexane thiol, or a combination thereof.

Functionalization of an enzyme can also be made using, for example, a haloalkane thiol that could react with an amine group attached to the enzyme. The haloalkane thiol can be a chloroalkane thiol. The chloroalkane thiol can be chloroethane thiol, chloropropane thiol, chlorobutane thiol, chloropentane thiol, chlorohexane thiol, or a combination thereof. Any of these haloalkane thiols can be used to modify the biocatalyst or enzyme to react with an alkene group attached to the substrate.

Preparation of Immobilized Biocatalysts and Enzymes

The immobilized biocatalyst or immobilized enzyme described herein can be prepared using a method comprising functionalizing a substrate with a thiol group; functionalizing a biocatalyst for hydrating carbon dioxide or a carbonic anhydrase with an alkene group; and reacting the thiol group of the substrate with the alkene group of the biocatalyst or carbonic anhydrase to form a moiety linking the substrate to the biocatalyst.

For example, a biocatalyst or enzyme functionalized with an alkene group can be placed in a container with a buffer solution and stirred. Then a substrate with a thiol group attached to the surface can be added with stirring. Once completely dispersed, a photoinitiator is added to the reaction mixture and the container is purged with nitrogen. The container is sealed and put in a UV-chamber until the reaction is complete. The product can be washed with buffer and dried using techniques known in the art.

Alternatively, a substrate with a thiol group attached to the surface can be placed in a container with reverse osmosis water. The mixture is purged with nitrogen and one or more redox agents or a potentiostat is used to control the redox behavior of the mixture. Next, a biocatalyst or enzyme with an attached alkene group can be added slowly and the reaction mixture is stirred until the reaction is complete. Once the reaction is complete, it is quenched with hard water. The resulting immobilized biocatalyst or enzyme is filtered, washed with water, and dried.

The immobilized biocatalyst or immobilized enzyme described herein can be prepared using a method comprising functionalizing a substrate with a thiol group; functionalizing a biocatalyst for hydrating carbon dioxide or a carbonic anhydrase with an alkene group; and reacting the thiol group of the substrate with the alkene group of the biocatalyst or carbonic anhydrase to form a moiety linking the substrate to the biocatalyst.

For example, a biocatalyst or enzyme functionalized with a thiol group can be placed in a container with a buffer solution and stirred. Then a substrate with an alkene group attached to the surface can be added with stirring. Once completely dispersed, a photoinitiator is added to the reaction mixture and the container is purged with nitrogen. The container is sealed and put in a UV-chamber until the reaction is complete. The product can be washed with buffer and dried using techniques known in the art.

Alternatively, a substrate with an alkene group attached to the surface can be placed in a container with reverse osmosis water. The mixture is purged with nitrogen and one or more redox agents or a potentiostat is used to control the redox behavior of the mixture. Next, a biocatalyst or enzyme with an attached thiol group can be added slowly and the reaction mixture is stirred until the reaction is complete. Once the reaction is complete, it is quenched with hard water. The resulting immobilized biocatalyst or enzyme is filtered, washed with water, and dried.

An enzyme functionalized with an alkene group can be attached to a substrate functionalized with a thiol group using a thiol-ene reaction.

Further, an enzyme having a thiol group or functionalized with a thiol group can be attached to a substrate functionalized with an alkene group using a thiol-ene reaction.

In particular, an allyl-PEG functionalized enzyme can be attached to a substrate functionalized with a thiol group using a thiol-ene reaction.

For example, an allyl-PEG functionalized carbonic anhydrase can be attached to a substrate functionalized with a thiol group using a thiol-ene reaction.

The thiol-ene reaction is a free radical addition of a thiol to a carbon-carbon double bond (or "ene") to give a thioether, as shown in Scheme 2.

Scheme 2

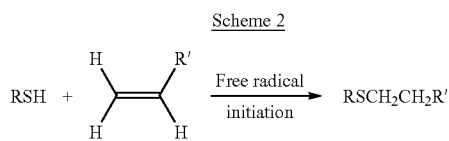

The thiol can be either an aryl or alkyl thiol. This thiol-ene reaction is called a click reaction because it is modular, wide in scope, gives very high yields, generates only inoffensive byproducts, and is stereospecific (Kolb, H. C., Finn, M. G., and Sharpless, K. B., Click Chemistry: Diverse Chemical Function from a Few Good Reactions, *Angew. Chem. Int. Ed.* 2001, 40, 2004-2021). The process requirements of click reactions include simple reaction conditions, readily available starting materials and reagents, the absence of solvent or use of environmentally benign solvents, and simple product isolation. These characteristics arise from a high thermodynamic driving force, usually greater than 20 kcal/mol, for the forward reaction.

The thiol-ene reaction can be initiated under mild conditions, for example, by photolysis or by redox chemistry to generate the requisite thiyl radical. In the ideal reaction, the thiyl radical adds to the ene to generate a carbon radical, which abstracts a hydrogen radical from thiol in a chain transfer process. The carbon center radical does not add to the ene to give a homopolymerization product. The net reaction is the combination of the thiol and ene functional groups to give a thioether link as shown in Scheme 3.

Scheme 3

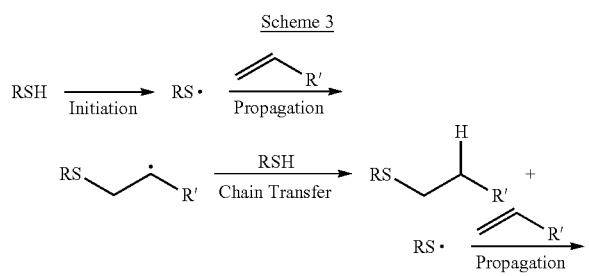

Immobilized enzymes can be obtained by reacting a substrate functionalized with alkenes with substrates functionalized with thiol groups (path a). Alternatively, enzymes containing thiol groups (e.g., cysteine residues) could be coupled with substrates functionalized with alkenes (path b). (Scheme 3)

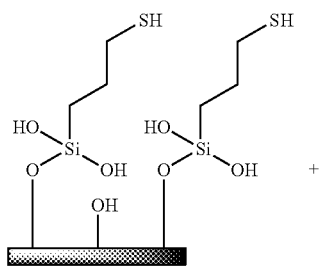

Scheme 4

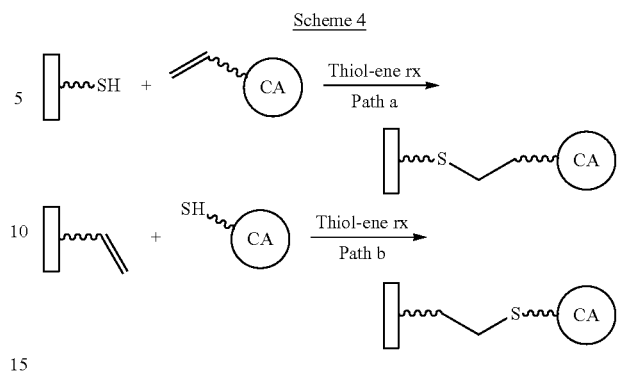

In a typical reaction, the thiol group of the substrate reacts with the alkene group attached to the enzyme or biocatalyst that catalyzes hydration of carbon dioxide using a photo-initiated or redox-initiated thiol-ene reaction.

When the reaction is photo-initiated, a light of the desired wavelength in the presence of a photoinitiator can be used. Exemplary photoinitiators are acetophenones (e.g., 2,2-dimethoxy-2-phenylacetophenone (Irgacure® 651), 1-[4-(2-hydroxyethoxy)-phenyl]-2-hydroxy-2-methyl-1-propane-1-one (Irgacure® 2959), bis(2,4,6-trimethylbenzoyl)-phenylphosphineoxide (Irgacure® 819), 1-hydroxy-cyclohexyl-phenyl-ketone (Irgacure® 184), etc.), peroxides (e.g., hydrogen peroxide, benzoyl peroxide, etc.), azo compounds (e.g., azobisisobutyronitrile, 1,1'-azobis(cyclohexanecarbonitrile, etc.), or a combination thereof.

When the reaction is redox-initiated, various combinations of oxidants and reducing agents can be used. Oxidants such as persulfates (e.g., sodium, potassium, and ammonium persulfate), peroxydicarbonates, sodium meta bisulfite (SMBS) and hydroperoxides can be used in combination with reducing agents such as tetramethyl ethylene diamine (TMEDA), ascorbic acid, formaldehyde sulfoxilate (SFS), sulfinic acid derivatives (Bruggolite® FF6M and Bruggolite® FF7). For example, ammonium persulfate/N,N,N',N'-tetramethylethylenediamine, triethyl boron (TEB)-di-tert-butylperoxide, peroxydicarbonates, tert-butylhydroperoxide (TBHP)/Bruggolite® FF7, TBHP/SFS, hydrogen peroxide/Bruggolite® FF7, ammonium peroxydisulfate (APS)/$Fe^{2+}$, hydrogen peroxide/$Fe^{2+}$, benzoyl peroxide/dimethylaniline, or a combination thereof can be used as redox initiators for this reaction.

A potential step chronoamperometry (potentiostatic) method for redox-initiated reaction can also be used. In this method the potential of the reaction solution is gradually increased until the thiol-ene reaction occurs.

Scheme 5 shows the reaction of the substrate functionalized with 3-mercaptosilane with a carbonic anhydrase having an allyl-PEG group attached.

-continued
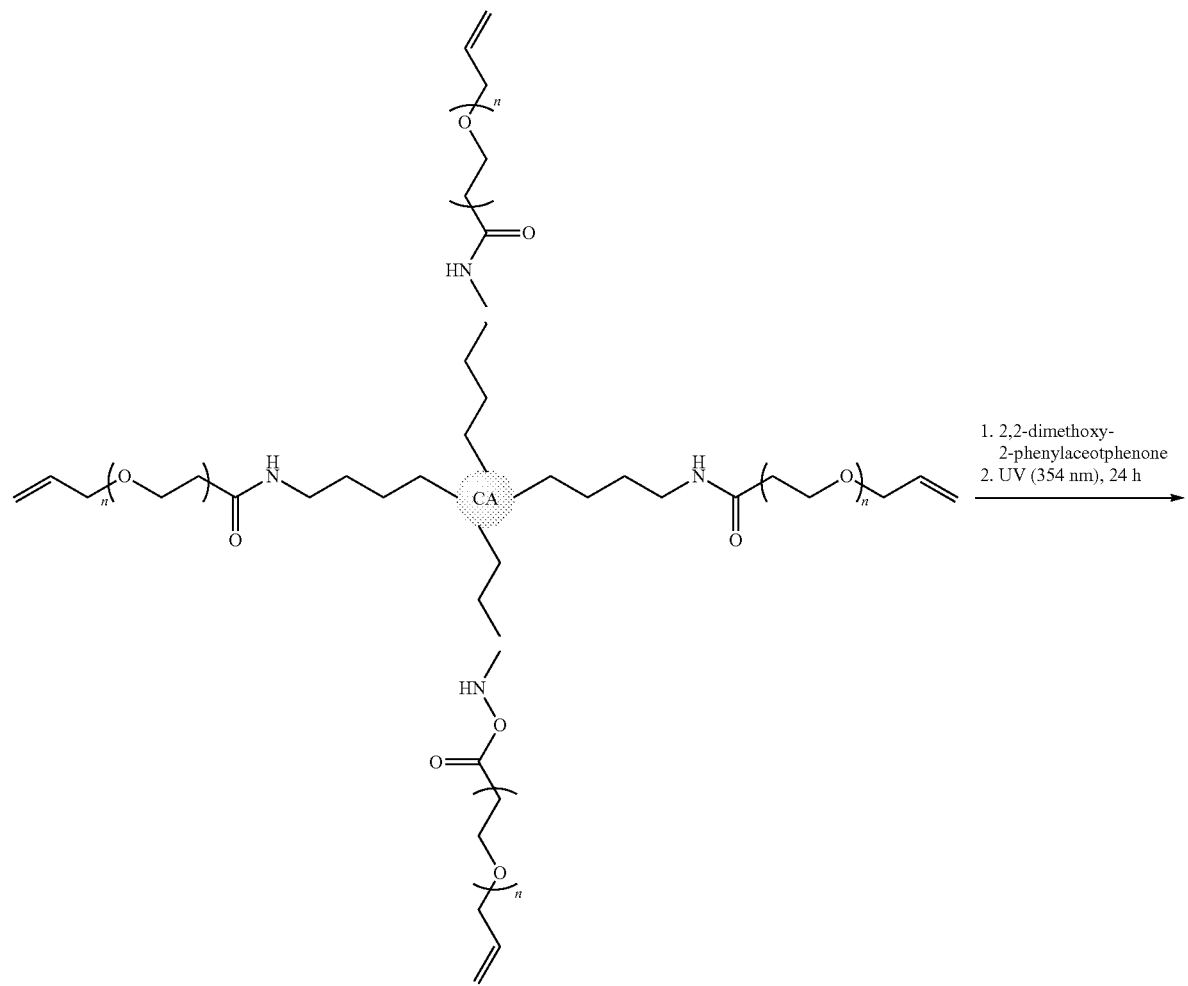
1. 2,2-dimethoxy-
   2-phenylaceotphenone
2. UV (354 nm), 24 h

-continued

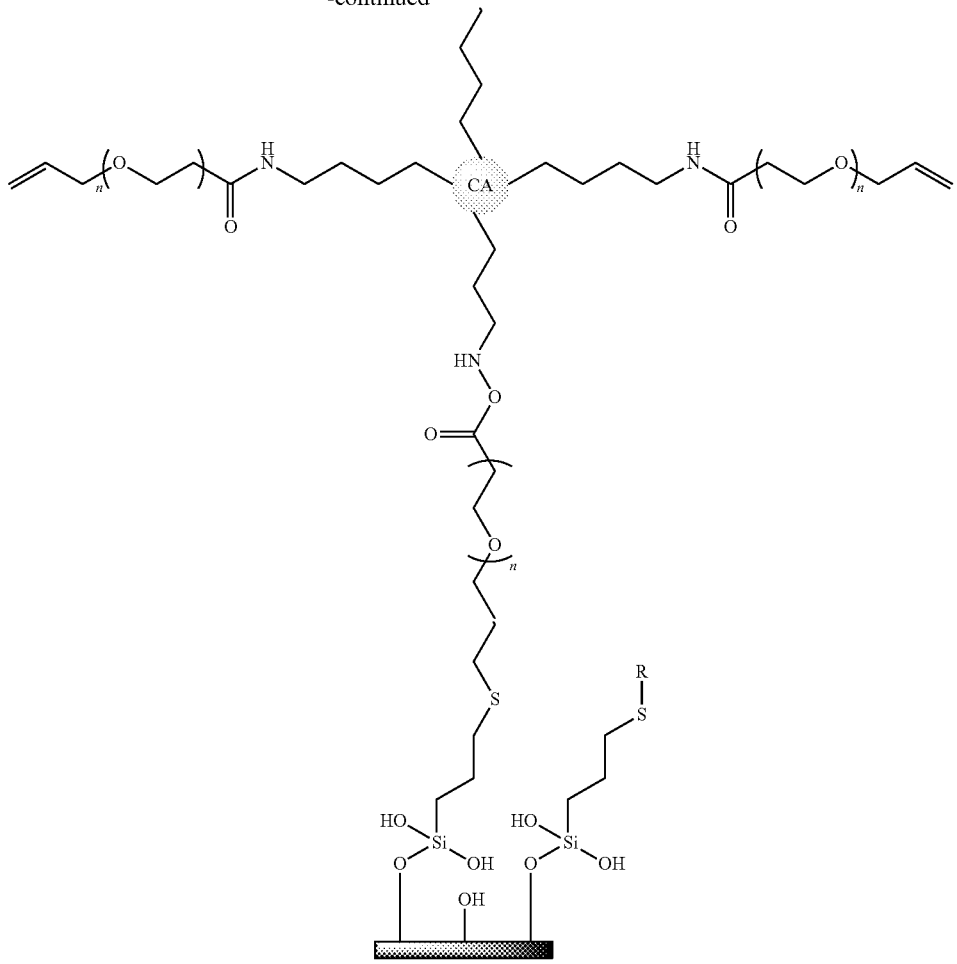

An optimized reaction provides greater than 97% yield over 24 hours in aqueous media. A different pH, salt concentration or the presence of oxygen does not affect the coupling reaction detrimentally.

Adjusting the coupling time alters the amount of enzyme that attaches to the substrate. Enzyme amount immobilized on the substrate is determined by monitoring the disappearance of soluble protein during the reaction. Ideally, the amount of enzyme immobilized on the substrate is verified independently via thermal gravimetric analysis.

The resulting products are washed with buffered aqueous solutions and stored in solution or dried. The retention of the enzyme post functionalization is monitored by analyzing the storage solutions for protein content using UV-Vis analysis. Over the course of a week, storage of the immobilized enzyme in a buffered solution resulted in no observable loss of enzyme.

When ceramic balls (⅛ in. diameter) are functionalized with carbonic anhydrase using this immobilization method, loadings as high as 4 mg/g are observed. This demonstrates applicability of this immobilization of biocatalysts or enzymes on substrates for packed bed reactions.

Figure 2:
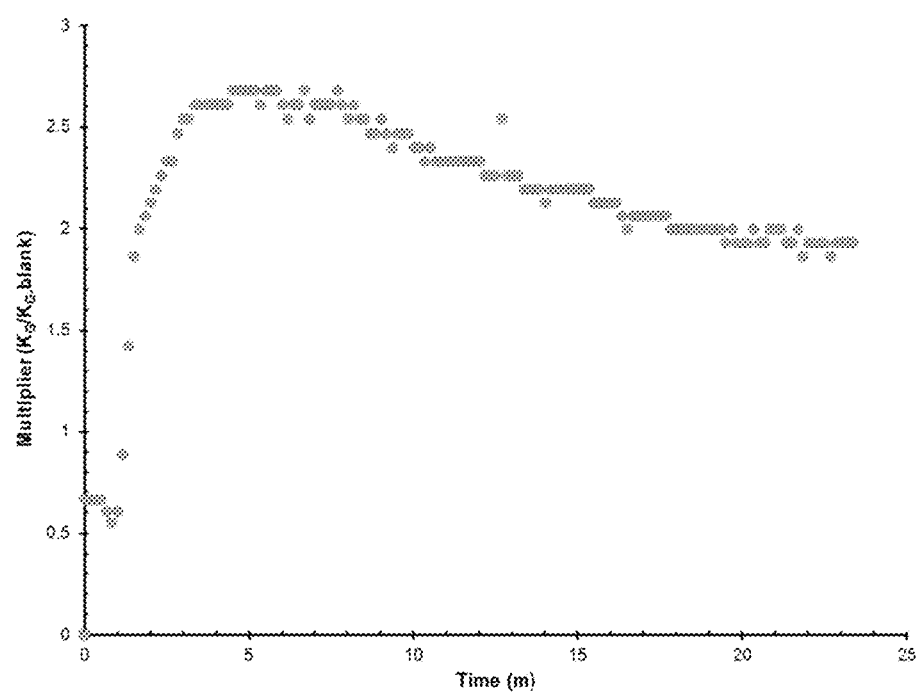
FIG. 2 is a graphical representation of the enzymatic activity of carbonic anhydrase functionalized ceramic balls, measured in a single-pass flow-through reactor.

As described in more detail in the examples, when immobilized carbonic anhydrase on ceramic balls were used to convert $CO_2$ to carbonic acid in a packed bed reactor using a flow-through single pass reactor (FIG. 1), a 2.4-fold enhancement in converted $CO_2$, as compared to an otherwise identical blank, was observed (Table 1 and FIG. 2). A bottle of test gas mixture 1 is connected to a calibrated mass flow controller 2 into an inlet tee 3 positioned below packed column reactor 4. The feed gas containing $CO_2$ flows upward through the packed column 4 and becomes partially depleted in $CO_2$ when absorbed into the down-flowing liquid. The treated gas exits the reactor at 5 and passes through a back pressure regulator 6. A flow indicating manual control valve 7 feeds a drying column 8 before delivery to a gas analyzer 9. The absorbent solution 10 is metered using a peristaltic pump 11, and a flow indicator 12 checks flow before sending gas to the packed column reactor 4. The rich liquid exits the reactor at 13 and passes into the waste reservoir 14 through a liquid seal. A vent line 15 maintains pressure balance between the supply reservoir 10 and the waste reservoir 14.

For fumed silica (i.e., CAB-O-SIL® EH-5), which is composed of discrete nanoparticles that agglomerate through hydrogen bonding into micro-aggregates, functionalized with carbonic anhydrase, loadings as high as 177 mg/g are observed. Surface functionalization of fumed silica particles, as well as ceramic balls, is confirmed using FTIR. Surface functionalization is then quantified using UV-Vis spectroscopic protein quantitation, and when ideally, tandem thermal gravimetric analysis (FIGS. 3-8).

These results show these biocatalysts or enzymes can be immobilized on microparticles and/or nanoparticles.

Preparation of Functionalized Substrate

The substrate can be functionalized with a thiol group. The substrate is described above.

The substrate can be functionalized with a thiol group by reacting the desired substrate with a mercaptoalkyl trialkoxysilane, a (mercaptoalkyl)alkyl dialkoxysilane, a mercaptoalkyl chlorosilane, or a combination thereof.

For example, a container can be charged with a substrate and an organic solvent with stirring. Next, a photoinitiator is added and stirred until the substrate is dispersed in the reaction mixture. Finally, a mercaptoalkyl trialkoxysilane, a (mercaptoalkyl)alkyl dialkoxysilane, or a mercaptoalkyl chlorosilane is added and the reaction mixture is stirred until the reaction is complete. The reaction solution is then filtered, the solid is washed with organic solvent and the product is dried using conventional drying techniques.

The organic solvent can be a non-chlorinated organic solvent such as toluene, hexanes, heptanes, and the like.

The substrate can also be functionalized with a thiol group by reacting the desired substrate with a haloalkane thiol group. The haloalkane thiol can be a chloroalkane thiol. The chloroalkane thiol can be chloroethane thiol, chloropropane thiol, chlorobutane thiol, chloropentane thiol, chlorohexane thiol, or a combination thereof.

For example, when the thiol functional group is (3-mercaptopropyl)trimethoxysilane, the reaction in Scheme 1.

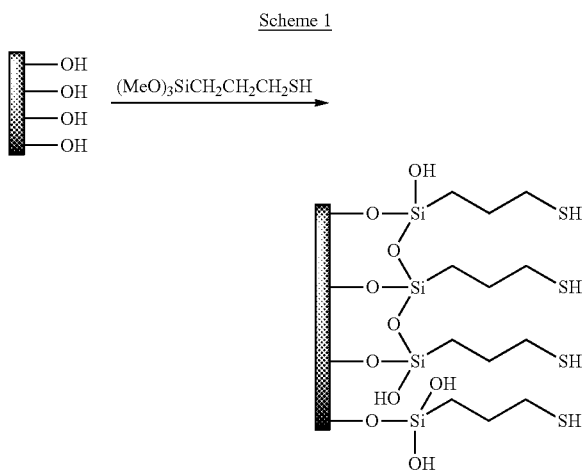

Scheme 1

While Scheme 1 depicts the surface of the substrate as covered with a partial monolayer of silane groups, the density of silane functionalization depends on the relative concentration of the substrate and silane. Thus, discrete attachments of silane groups, a partial monolayer, or a monolayer of silane groups can form on the surface of the substrate. This could be used to prepare thiol functionalized metal oxides including titanium oxide and aluminum oxide, as well as iron based materials including iron oxide, steel, and stainless steel.

The surface of the substrate can be treated before functionalization with a thiol group to enhance the reaction with the precursor of the thiol group. The substrate can optionally undergo an etching step before it is functionalized with the thiol group. One advantage of an etching step is that it serves to increase the surface area and number of functional groups on the substrate, which facilitates a more effective functionalization process.

Typically, the etching reagent comprises an acid. Hydrogen fluoride is a preferred acid, and is particularly preferred where the substrate comprises a ceramic material.

The substrate can be prepared for reaction by contacting the substrate with acid, followed by washing and drying before use. The acid used can be a strong acid such as hydrochloric acid, sulfuric acid, phosphoric acid, or a combination thereof. The acid could also be a weak acid such as hydrofluoric acid.

The acid for contacting the substrate can be hydrofluoric acid. This process is followed by washing with water and drying using conventional drying techniques.

When the acid is hydrofluoric acid, the substrate can be ceramic spheres.

The etching reagent can comprise an oxidant. Preferred oxidants include hydrogen peroxide, ammonium hydroxide, and mixtures thereof. Mixtures of hydrogen peroxide and ammonium hydroxide typically have a mass ratio of from about 1:4 to about 4:1, more typically a ratio of about 1:1.

The substrate can also be contacted with a mixture of hydrogen peroxide and ammonium hydroxide. The reaction can be heated and once complete, the substrate can be washed with water and dried using conventional methods.

When a mixture of hydrogen peroxide and ammonium hydroxide is used, the substrate can be ceramic spheres.

In some cases, the etching step will comprise contacting the substrate with a reducing agent followed by contacting the substrate with an oxidant.

In the case of stainless steel, treatments such as washing, polishing, descaling, and sand blasting can be used to pretreat the surface. Typical descaling solutions may comprise aqueous solutions of hydrofluoric and/or nitric acid.

When the substrate is functionalized with an alkene group the following reactions can occur. Even though specific chain length reagents are shown in the figures, a person skilled in the art would have known that different reagents having the same functional groups could have been used to prepare the substrates having an alkene group attached to its surface.

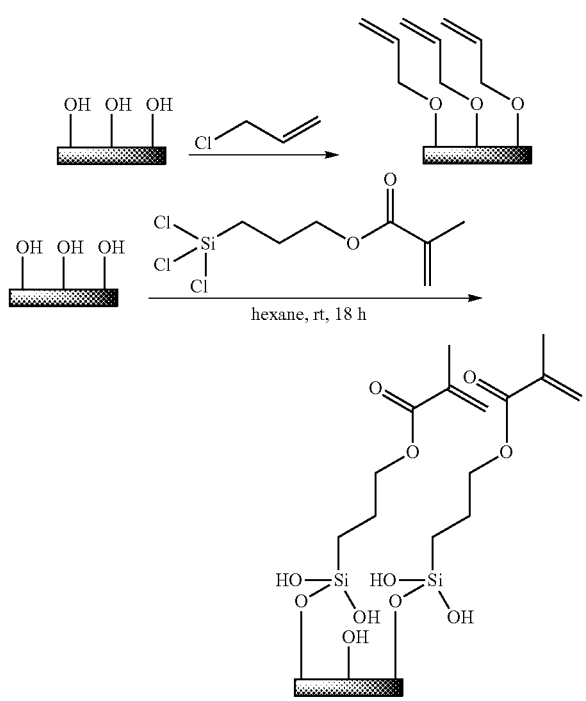

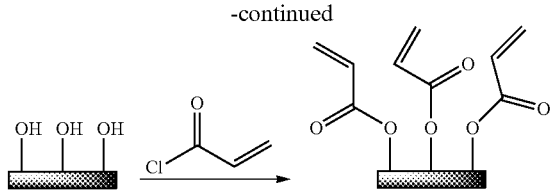

Processes and Systems for Removal of Carbon Dioxide

Immobilized biocatalysts, wherein a carbonic anhydrase or a biocatalyst that catalyzes hydration of carbon dioxide is attached to a substrate, can be used to catalyze a process for removing $CO_2$ from a $CO_2$-containing gas.

The process for removing $CO_2$ from a $CO_2$-containing gas can comprise contacting a gas comprising $CO_2$ with a water-containing liquid and an immobilized biocatalyst or immobilized enzyme described herein to catalyze hydration of the $CO_2$ with water and form hydrogen ions and bicarbonate ions.

Typically, the process comprises contacting a liquid with a $CO_2$-containing gas to promote diffusion of the $CO_2$ into the liquid. The liquid can then be contacted with an immobilized biocatalyst to catalyze hydration of the $CO_2$, thereby forming a treated liquid comprising hydrogen ions and bicarbonate ions.

Generally, the enzyme can catalyze the hydration reaction that is the first step of a two-step sequence:

$$CO_2 + H_2O \rightarrow H^+ + HCO_3^- \quad (1)$$

$$CO_3^{2-} + H^+ \rightarrow HCO_3^- \quad (2)$$

By using carbonic anhydrase to catalyze $CO_2$ hydration [reaction (1)], the rate of conversion of $CO_2$ into the bicarbonate form is accelerated.

The $K_{eq}$ for the hydration reaction at 25° C. is $1.7 \times 10^{-3}$; the reaction at equilibrium under acidic and neutral conditions favors the $CO_2/H_2O$ side of the equation. In reaction (2), under more basic conditions the carbonate captures the proton produced in reaction (1) and creates a driving force to produce more bicarbonate.

Carbonic anhydrase can also be used to catalyze the dehydration of the bicarbonate back into $CO_3^{2-}$, $CO_2$, and water. The carbonate can be recycled back to the first reactor where the dehydration of $CO_2$ occurs. For example, the chemistry for dehydration of $NaHCO_3$ is as follows:

$$2NaHCO_3 \rightarrow Na_2CO_3 + H_2O + CO_2 \quad (3)$$

Upon heating, bicarbonate releases the $CO_2$ and water and forms carbonate ions that can be recycled to the hydration reaction. The CA in the dehydration reactor is similar to that in the $CO_2$ hydration unit and should increase the rate of this reaction. At standard temperature and pressure, $CO_2$ has a solubility of about 1.8 grams/liter; thus a system allowing for rapid transfer of $CO_2$ to the aqueous phase is desired.

The sodium can be replaced by another cation (e.g., alkali metal, alkaline earth metal, etc.). The metal can be selected so that the resulting carbonate is soluble in the aqueous solution.

The carbonic anhydrase can also be used to accelerate the capture of carbon dioxide with amines or ammonia. The amine or ammonia can be placed in the liquid contacting the carbon dioxide stream and when carbon dioxide is hydrated it reacts with an amine or ammonia, forming a carbonate. When the liquid of the system contains amines, this reaction can occur.

In some cases, both a carbonate and an amine are present in the liquid contacted with the carbon dioxide stream. In that case, both carbonates and carbamates are produced from the various reactions with carbon dioxide.

When the liquid contains an amine, the amine can be methylamine, ethylamine, propylamine, iso-propylamine, butylamine, iso-butylamine, sec-butylamine, tert-butylamine, pentylamine, iso-pentylamine, sec-pentylamine, tert-pentylamine, hexylamine, iso-hexylamine, sec-hexylamine, tert-hexylamine, ethylenediamine, (2-methylbutyl)amine, 2-aminopentane, 3-(tert-butoxy)propylamine, 2-amino-6-methylheptane, 1-ethylpropylamine dimethylamine, diethylamine, dipropylamine, dibutylamine, dipentylamine, dihexylamine, N-ethylmethylamine, N-isopropylmethylamine, N-butylmethylamine, N-ethylisopropylamine, N-tert-butylmethylamine, N-ethylbutylamine, 3-isopropoxypropylamine, chloro(diethylamino)dimethylsilane, 2,2'-(ethylenedioxy)bis(ethylamine), 1,3-bis(chloromethyl)-1,1,3,3-tetramethyldisilazane, N-tert-butylisopropylamine, N,N-diethyltrimethylsilylamine, di-sec-butylamine, trimethylamine, triethylamine, tripropylamine, tributylamine, dimethylpropylamine, diethylpropylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine, or a combination thereof.

System Design

The system used to hydrate carbon dioxide gas in a gas stream to form bicarbonate ions can use a variety of reactors, including a packed bed, a fluidized bed, or a continuous stirred tank. When a packed or fluidized bed reactor is used, the gas and liquid streams entering the reactor can be in a co-current or counter current configuration. For example, in a co-current system, the gas and liquid streams could enter the reactor in the form of microbubbles of gas in the liquid stream.

The packing of the reactors preferably comprises the immobilized biocatalyst or immobilized carbonic anhydrase as described above.

The configuration in the reactor could be similar to a tray style distillation column wherein the packing material includes a membrane comprising the immobilized carbonic anhydrase is oriented to maximize the surface contact with the gas and liquid streams (e.g., by folding the membrane back on itself in a serpentine configuration).

Figure 9A:
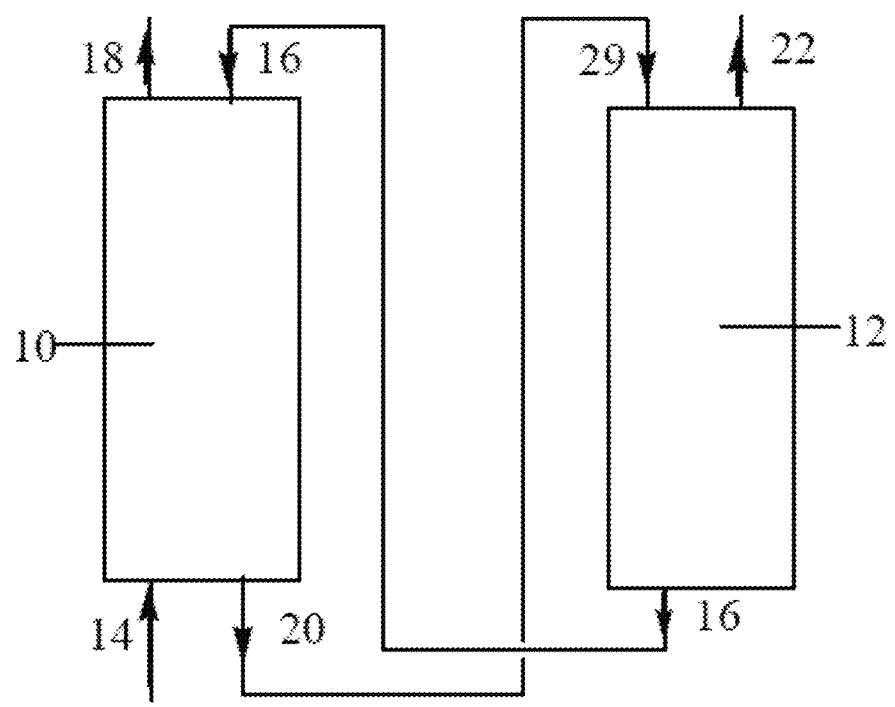
FIGS. 9A and 9B are schematics of a $CO_2$ absorber coupled with a $CO_2$ stripper.

In one particular system, a two unit continuous flow system can be used to hydrate $CO_2$ gas to form bicarbonate ions in a $CO_2$ absorber and dehydrate the bicarbonate ions to $CO_2$, water, and carbonate ions in a $CO_2$ stripper. In some instances, the units have a packed tower design. A schematic diagram of this two unit system including an absorber 10 and a stripper 12 is depicted in FIG. 9A. A $CO_2$ gas stream 14 enters the bottom of the absorber 10, and a liquid stream 16 enters the top portion of the absorber 10. The liquid stream 16 is distributed over the top of the immobilized biocatalysts (not shown) in the middle portion of the absorber 10 by a distributor (not shown). The liquid stream 16 wets the surfaces of the immobilized biocatalysts and flows downward through the absorber 10 while the $CO_2$ gas stream 14 flows upward through the suspended immobilized biocatalysts countercurrent to the flow of the liquid. The immobilized biocatalysts provide an area of contact between the liquid and gas phases, and include carbonic anhydrase immobilized on the substrate. The $CO_2$ in the gas stream is absorbed by the liquid, and the treated gas stream 18 leaves the top of the absorber. The liquid is enriched in $CO_2$ as it flows down the column, bicarbonate is formed, and the treated liquid stream 20 leaves the bottom of the absorber. The treated liquid stream 20 is pumped to a top portion of the stripper 12, and is distributed by a distributor (not shown) over packing. The bicarbonate within the liquid stream 20 is converted to carbon dioxide, water and carbonate. Reaction rates of this reaction to produce $CO_2$ can be increased by adding heat, reducing pressure, immobilizing carbonic anhydrase in the stripper, and by increasing the rate of removal of $CO_2$ from the stripper 12 by operating at below atmospheric pressure. The water and carbonate can be recycled and combined with the liquid stream 16 entering the absorber 10, and the carbon dioxide leaves the top of the stripper as gas stream 22 and can be further processed as desired.

Alternatively, the absorber can have immobilized carbonic anhydrase in suspension and can be contacted with a regular gas flow or microbubble $CO_2$ gas and an aqueous carbonate solution to allow for increased surface area between the gas and liquid for transport of the $CO_2$ gas into the aqueous carbonate solution.

When the substrate is a microparticle or nanoparticle, the immobilized carbonic anhydrases described herein can be suspended in the reactor.

For example, when the nanoparticulate substrate with immobilized carbonic anhydrase is dispersed well in aqueous solutions, a stable suspension results, providing high surface area, allowing for high enzyme loadings and a 4-fold enhancement in converted $CO_2$, as compared to an otherwise identical blank.

Figure 9B:
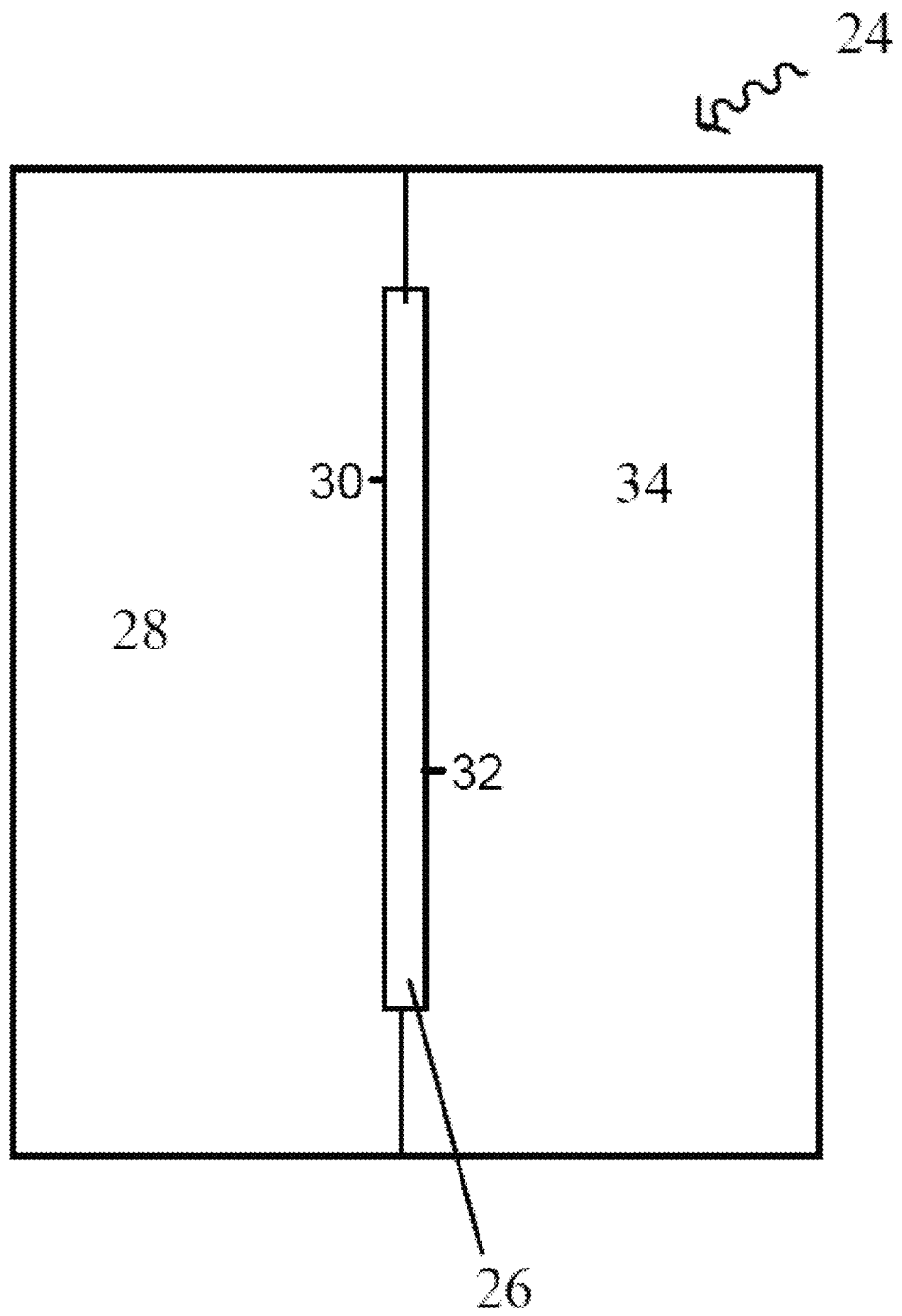

The system can also include a reactor 24 as shown in FIG. 9B having a membrane 26 wherein a gas stream 28 containing $CO_2$ is in contact with a first surface 30 of the membrane and an aqueous carbonate stream 34 is on a second surface 32 of the membrane. The membrane is permeable to at least the $CO_2$ gas, but is either impermeable to the aqueous carbonate stream 34 or the first surface 30 is impermeable to the stream 34. The membrane 26 can support an immobilized carbonic anhydrase as described herein. The $CO_2$ gas in the gas stream 28 can interact with the immobilized carbonic anhydrase and the stream 34 and be converted to bicarbonate. The bicarbonate can be absorbed by the stream 34 in contact with the immobilized enzyme. The membrane material can be a polysaccharide, an ion exchange resin, a treated silicon oxide, a porous metal structure, a carbon rod or tube, a graphite fiber, a silica bead, a cellulose membrane, a gel matrix (e.g., a polyacrylamide gel, a poly(acryloyl morpholine) gel, a nylon mesh and the like). High surface area/volume membrane systems that can be used in this configuration are disclosed in U.S. Pat. No. 6,524,843.

The stripper can be the site where bicarbonate is converted into $CO_2$ and water.

The stripper can alternatively have carbonic anhydrase immobilized on standard reactor packing materials or the substrate described herein and a feed of bicarbonate solution from the absorber. Reaction rates of this reaction to produce $CO_2$ can be increased by adding heat and the removal of $CO_2$ from the stripper could be increased by operating at below atmospheric pressure.

These system designs can be combined in different configurations depending on the specific application or gas stream to be treated. For example, the system specifications can be tailored to the $CO_2$ content of the feed stream and the overall purity, recovery, and contaminant levels required for the product streams along with the temperature and pressure requirements of both streams. The use of immobilized enzymes increases the range of system operating conditions as compared to the corresponding free enzyme.

A packed tower as described herein can be used as the absorber in conjunction with a membrane reactor as described herein as the stripper.

Alternatively, a membrane reactor as described herein can be used as the absorber and a packed tower as described herein can be used as the stripper.

Figure 10:
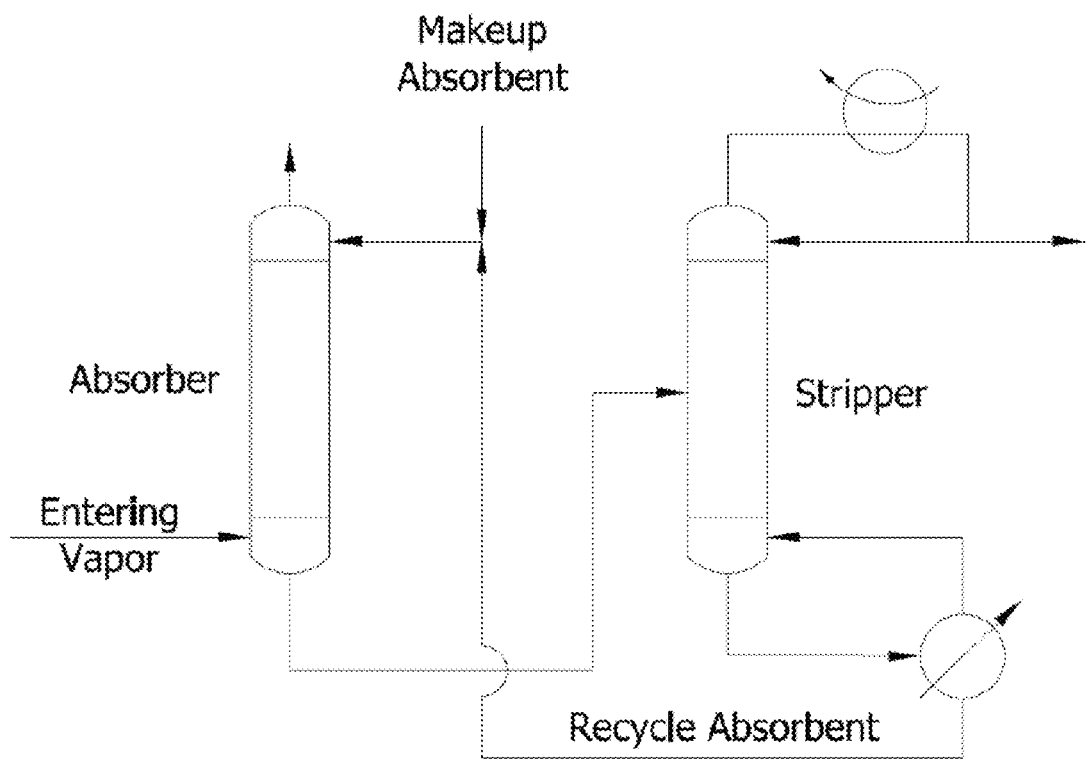
FIG. 10 is a schematic of a carbon capture system having an absorber and a stripper.

Also, the system design can be generally as depicted in FIG. 10. For example, the carbon capture process unit comprises a standard absorption unit and a stripping (reactive distillation) unit. The core components of the carbon capture system (CCS) are an absorbing unit operation, a stripping unit operation, and a heat exchange component between the two unit operations. Peripheral equipment could include standard control hardware and software, flow monitoring and regulation (e.g., control valves, flow meters), pumps, pH monitoring (e.g., pH meters), temperature monitoring (e.g., temperature monitors), or any combination thereof. The additional equipment could provide means for monitoring and controlling the process.

The system can comprise a plurality of reaction vessels, wherein two or more reaction vessels contain the immobilized biocatalysts described herein.

DEFINITIONS

Unless otherwise indicated, an "alkyl" group as described herein alone or as part of another group is an optionally substituted linear saturated monovalent hydrocarbon radical containing from one to twenty carbon atoms and preferably one to twelve carbon atoms, or an optionally substituted branched saturated monovalent hydrocarbon radical containing three to twenty carbon atoms, and preferably three to eight carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The term "cycloalkyl" as used herein denotes optionally an optionally substituted cyclic saturated monovalent bridged or non-bridged hydrocarbon radical containing from three to eight carbon atoms in one ring and up to 20 carbon atoms in a multiple ring group. Exemplary unsubstituted cycloalkyl groups include cyclopropyl, cyclobutyl, cyclopentyl, cyclohexyl, cycloheptyl, cyclooctyl, adamantyl, norbornyl, and the like.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as methylene ($—CH_2—$) or ethylene ($—CH_2CH_2—$), and arylene denotes a bivalent aryl group such as o-phenylene, m-phenylene, or p-phenylene. For clarity, addition of the -ene suffix is not intended to alter the definition of the principal word other than denoting a bivalent radical. Thus, continuing the example above, alkylene denotes an optionally substituted linear saturated bivalent hydrocarbon radical.

The term "heteroaryl," as used herein alone or as part of another group, denotes an optionally substituted monovalent monocyclic or bicyclic aromatic radical of 5 to 10 ring atoms in protonated or unprotonated form, where one or more, preferably one, two, or three, ring atoms are heteroatoms independently selected from N, O, and S, and the remaining ring atoms are carbon. Exemplary heteroaryl moieties include benzofuranyl, benzo[d]thiazolyl, benzo[d]thiazolium, isoquinolinyl, isoquinolinium, quinolinyl, quinolinium, thiophenyl, imidazolyl, imidazolium, oxazolyl, oxazolium, furanyl, thiazolyl, thiazolium, pyridinyl, pyridinium, furyl, thienyl, pyridyl, pyrrolyl, pyrrolidinium, indolyl, indolinium, and the like.

The term "heterocyclo," as used herein alone or as part of another group, denotes a saturated or unsaturated monovalent monocyclic group of 4 to 8 ring atoms in protonated or unprotonated form, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, pyrrolidinium, piperidino, piperidinium, morpholino, morpholinium, piperazino, piperazinium, succinimide, and the like. In some cases, the heterocyclo can be a bivalent radical wherein the hydrogen is removed from each of two atoms in the heterocyclo group.

Having described the invention in detail, it will be apparent that modifications and variations are possible without departing from the scope of the invention defined in the appended claims.

EXAMPLES

The following non-limiting examples are provided to further illustrate the present invention.

Example 1

Functionalization of Carbonic Anhydrase with Allyl-PEG-Succinimide or N-Acryloxysuccinimide Carbonic anhydrase (CA) could be functionalized with allyl groups by coupling allyl-succinimides to the amine groups of CA. The example below illustrates the coupling of Novozymes NS81239 CA and allyl-PEG-succinimide.

A 150 mL beaker was filled with 40 mL of 41.4 mg/mL dialyzed Novozymes NS-81239 CA and 40 mL of 200 mM phosphate buffer, pH 7.5. A Teflon stir bar was added and the solution was stirred to homogenize. Allyl-PEG succinimide (0.99 mL; $M_w$=500) (30:1 molar ratio of allyl-PEG-succinimide to CA) was then added dropwise to the beaker with stirring. The reaction mixture was stirred for 2 hours at room temperature. The solution was purified by dialysis in dialysis tubing with a MWCO of 6000-8000 Da against 5 mM phosphate buffer, pH 7.5 for two days, changing the buffer twice. The allyl-PEG functionalized CA was then lyophilized to dryness before use. The extent of functionalization could be manipulated by changing the amount of allyl-PEG succinimide used in the above procedure.

A similar procedure was used for the functionalization of Novozymes CA with N-acryloxysuccinimide. In this analogous procedure, N-acryloxysuccinimide was dissolved in minimal amounts of dimethyl sulfoxide and then added dropwise to the enzyme in phosphate buffer. Alternatively, N-acryloxysuccinimide powder was added directly to the enzyme/phosphate buffer solution, where it dissolved over the course of a few minutes.

Example 2

HF Etching of Ceramic Balls

A 2000 mL plastic bucket was charged with 1300 g of ⅛ inch Tipton ceramic balls, and subsequently covered with 1 L of 15% aqueous HF solution. The solution was manually stirred using a large plastic spatula every 30 minutes for the first 3 hours. Then the solution was covered with a plastic lid and allowed to sit overnight at room temperature and ambient pressure. After 24 hours, the HF solution was decanted, and the ceramic spheres were washed three times over a sifter with reverse osmosis treated water. After washing, the spheres were dried at 90° C. for 24 hours before further use.

Example 3

Hydrogen Peroxide/Ammonium Hydroxide Etching of Ceramic Balls

A 2500 mL Pyrex® beaker was charged with 1300 g of ⅛ inch Tipton ceramic balls, and subsequently covered with 900 mL of water, 300 mL of hydrogen peroxide (30% aqueous solution), and 300 mL of ammonium hydroxide (28-30% ACS). The solution was heated on a hot plate to 80° C. and manually stirred every 30 minutes for 3 hours. After 3 hours, the etching solution was decanted, and the ceramic spheres were washed three times over a sifter with reverse osmosis treated water. After washing, the spheres were dried at 80° C. for 24 hours before further use.

Example 4

Functionalization of Ceramic Balls with (3-Mercaptopropyl)TrimethoxySilane

Figure 3:
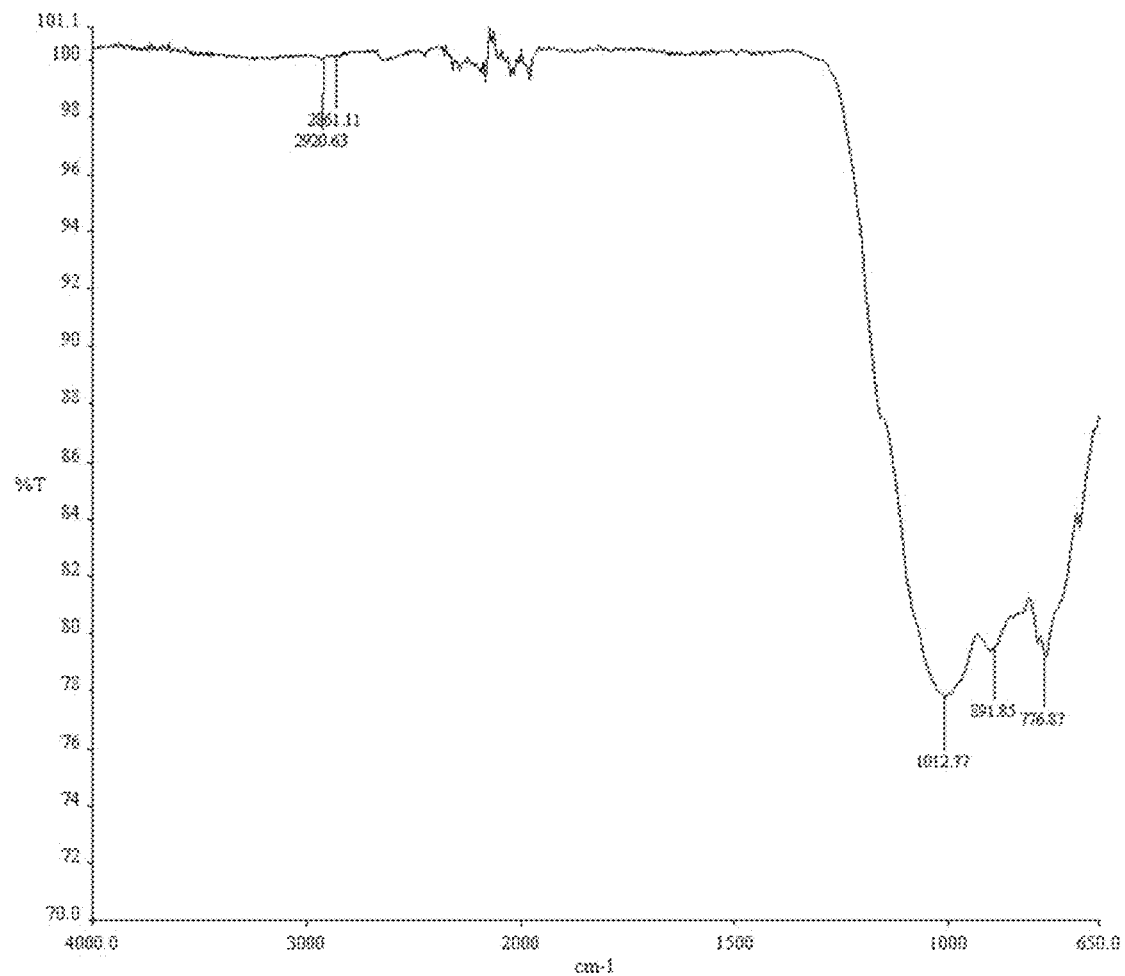
FIG. 3 is a Fourier transform infrared (FTIR) spectrum of thiol-functionalized ceramic balls.

In a typical example, a 500 mL round-bottom flask was charged with Tipton ceramic balls (65 g) and 95 mL of anhydrous toluene under mechanical stirring. The reaction mixture was then purged for 15 minutes under nitrogen. Next, (3-mercaptopropyl)trimethoxysilane (5 ml; 27.0 mM) was added to the solution dropwise via syringe. The reaction mixture was then stirred at room temperature for 24 hours. After 24 hours, the reaction solution was filtered over a sifting tray and was subsequently washed three times with 25 mL of hexane. The product was dried at room temp for 24 hours and then stored at 70° C. for 24 hours. FTIR ($cm^{-1}$): 776, 891, 1012, 2861, and 2920 (FIG. 3).

Example 5

Figure 5:
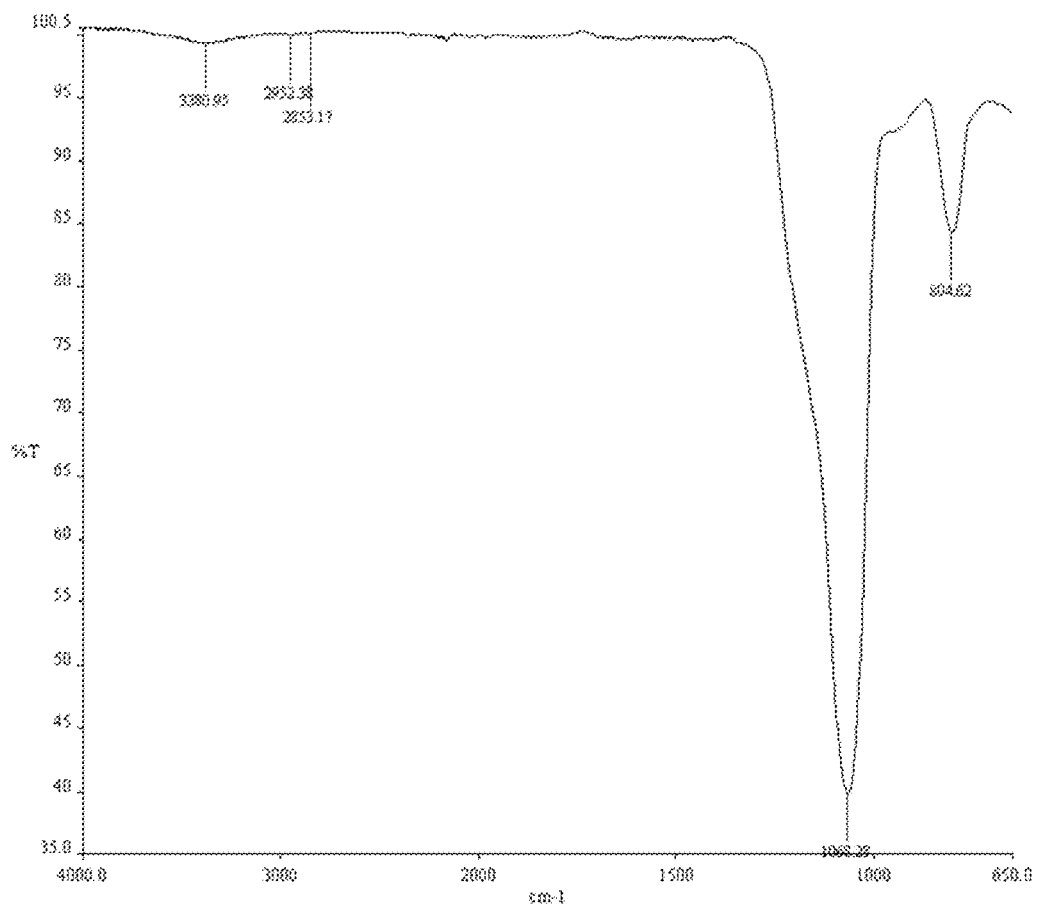
FIG. 5 is a FTIR spectrum of thiol-functionalized fumed silica nanoparticles.
Figure 6:
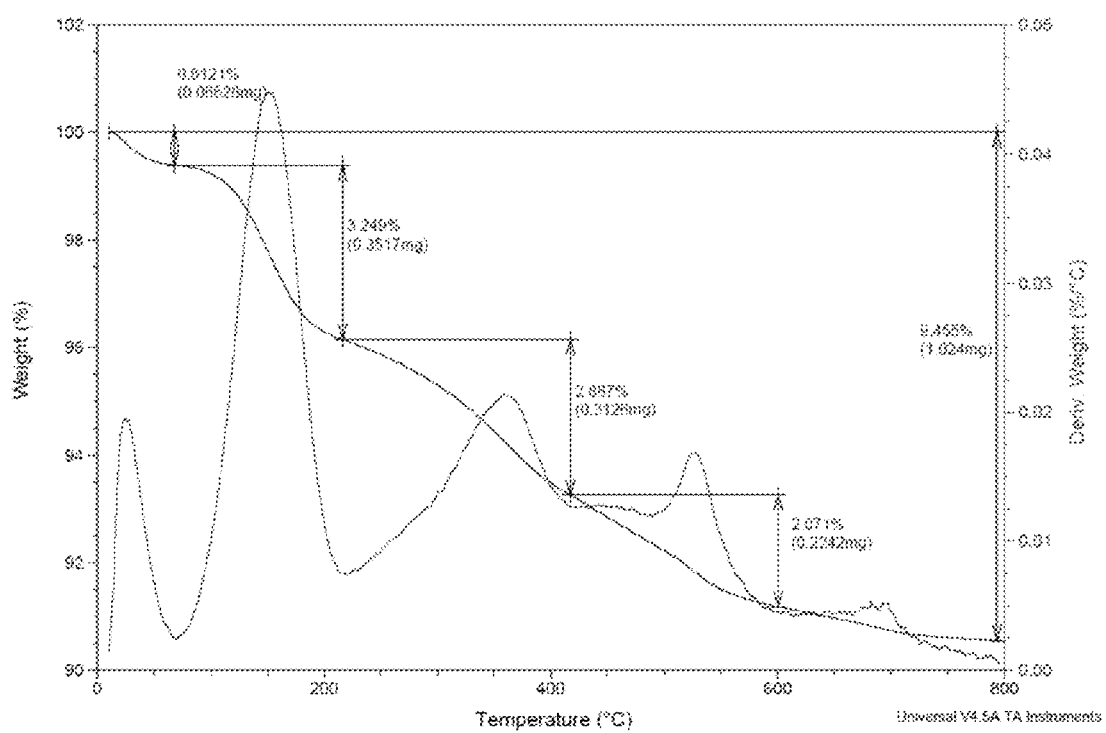
FIG. 6 is a graphical representation of thermogravimetric analysis of thiol-functionalized fumed silica.

Functionalization of Fumed Silica Nanoparticles with (3-Mercaptopropyl)-Trimethoxysilane In a typical example, a 2000 mL three-neck flask was charged with 600 mL of anhydrous toluene and then 30 g of fumed silica nanoparticles (CAB-O-SIL® EH-5) were slowly added under mechanical stirring. After addition, the solution was stirred vigorously for 1 hour to effectively disperse the fumed silica particles. After 1 hour, 30 mL of (3-mercaptopropyl)trimethoxysilane (161 mM) was added to the solution dropwise via syringe. The reaction mixture was then stirred vigorously at room temperature for 24 hours. After 24 hours, the reaction solution was filtered and the fumed silica particles were subsequently washed three times with 100 mL of toluene and then three times with 100 mL of hexane. The product was dried at room temperature for 24 hours and then stored at 70° C. for 24 h. FTIR (cm$^{-1}$): 804, 1068, 2853, 2952, and 3380 (FIG. 5).

Example 6

Figure 4:
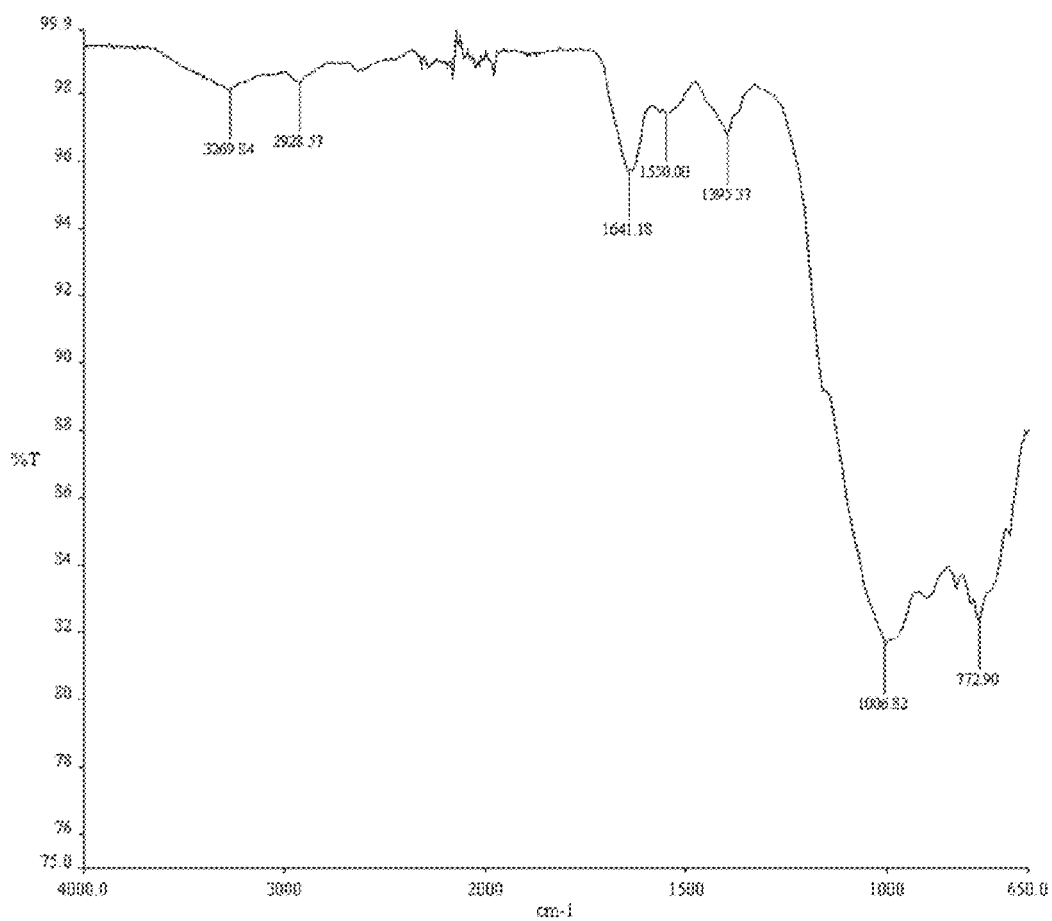
FIG. 4 is a FTIR spectrum of allyl-PEG-carbonic anhydrase functionalized ceramic balls synthesized via redox initiated thiol-ene reaction.

Thiol-Ene Reaction of Thiol Functionalized Ceramic Balls with Allyl-PEG Functionalized Carbonic Anhydrase via Redox Initiation A 250 mL round-bottom flask was charged with thiol functionalized Tipton ceramic balls (65.07 g) and 25 mL of reverse osmosis water. The mixture was then purged with nitrogen for 15 minutes, after which time ammonium persulfate (60 mg, 0.26 mmol) and N,N,N',N'-tetramethylethylene diamine (60 μL, 0.40 mmol) were added. Next, an allyl-PEG functionalized thermophilic derivative of carbonic anhydrase (0.9122) in 2 mL of water was added dropwise via syringe over the course of 1.5 hours. The reaction mixture was stirred at room temperature for 24 hours, and was subsequently quenched with hard water. The ceramic balls were filtered and washed three times with water. The amount of bound protein was determined via UV-Vis spectroscopic analysis. Loadings as high as 3 mg of CA/g of ceramic balls were observed for 24 hour initiation times. FTIR (cm$^{-1}$): 772, 1006, 1395, 1550, 1641, 2928, and 3269 (FIG. 4).

Example 7

Thiol-Ene Reaction of Thiol Functionalized Ceramic Balls with Allyl-PEG Functionalized Carbonic Anhydrase Derivative Via Photo-Initiation A 500 mL screw top jar was charged with thiol functionalized Tipton ceramic balls (65.00 g) and a solution of an allyl-PEG functionalized carbonic anhydrase (0.800 mg) in 16 mL of a 10 mM phosphate buffer (pH=7). Next, 12 mg (0.047 mmol) of 2,2-dimethoxy-2-phenylacetophenone (Irgacure 651) was added to the reaction mixture and the solution was purged with nitrogen for 15 minutes. The reaction vessel was sealed and put in a UV chamber (365 nm) for 24 hours. After 24 hours, the reaction was quenched with hard water, filtered via gravity filtration, and rinsed three times with 50 mL of 1.2 M $K_2CO_3$/0.8 M $KHCO_3$ solution (pH=10.2). The amount of bound protein was determined via UV-Vis spectroscopic analysis. Loadings as high as 4 mg of CA/g of ceramic balls were observed for 24 hour initiation times. FTIR (cm$^{-1}$): 844, 992, 1361, 1450, 1663, and 3147.

Example 8

Figure 7:
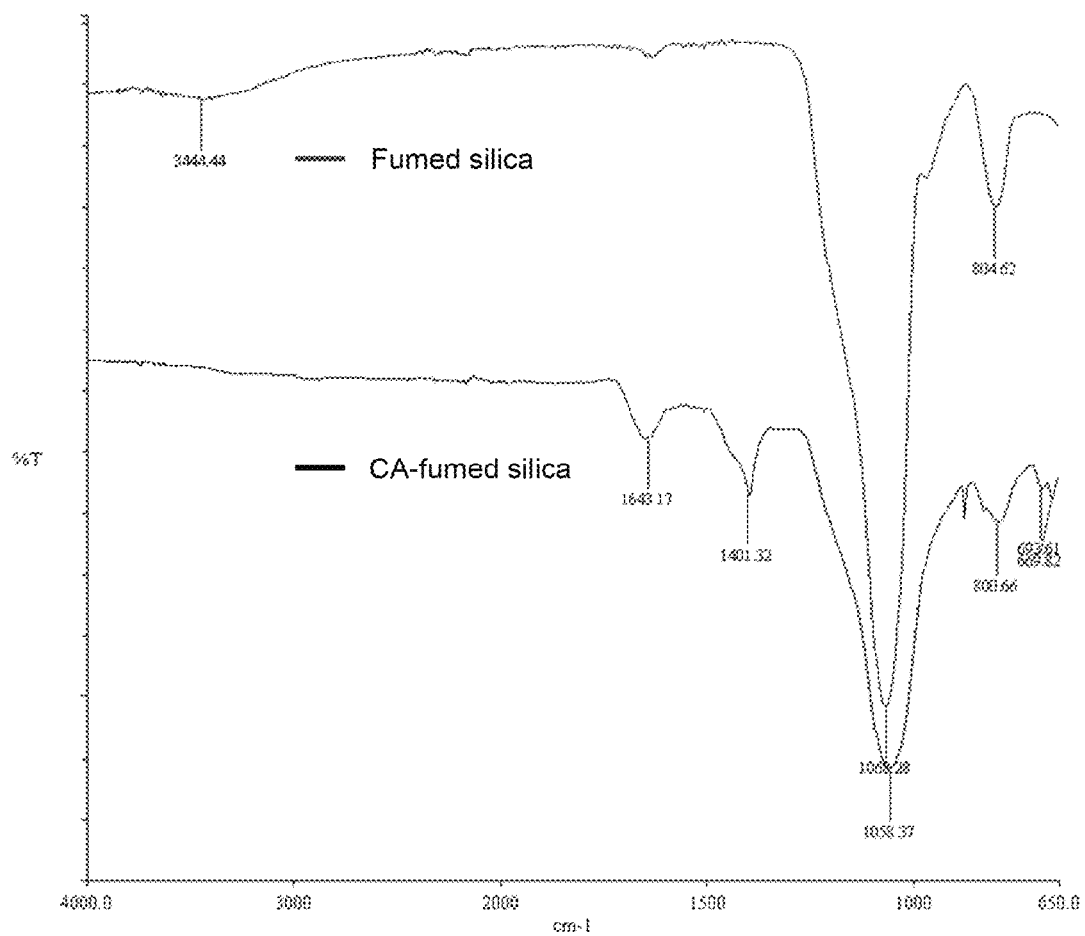
FIG. 7 is a FTIR spectrum of fumed silica nanoparticles (top line) overlayed on the FTIR spectrum of carbonic-anhydrase functionalized fumed silica nanoparticles (bottom line).
Figure 8:
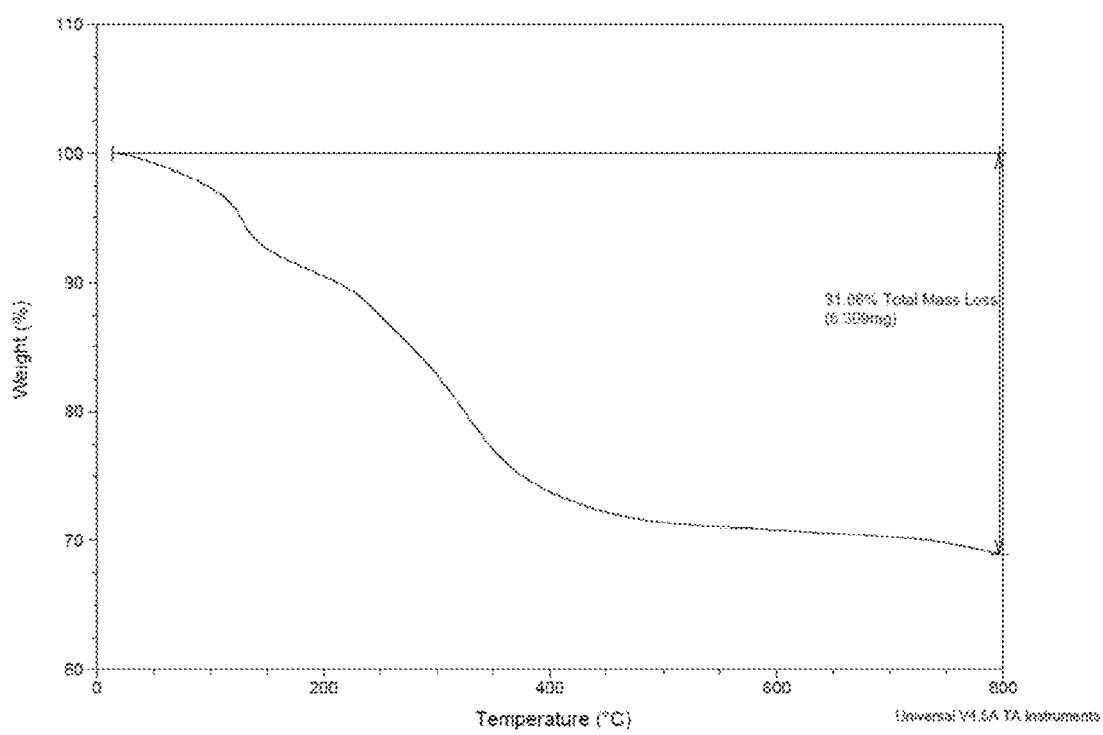
FIG. 8 is a graphical representation of thermogravimetric analysis of carbonic anhydrase functionalized fumed silica nanoparticles.

Thiol-Ene Reaction of Thiol Functionalized Fumed Silica Nanoparticles with Allyl-PEG Functionalized Carbonic Anhydrase Via Photo-Initiation In a typical procedure, 150 mL of 10 mM phosphate buffer was added to a 500 mL glass screw top vial. Next, 6 g of an allyl-PEG functionalized carbonic anhydrase in 30 mL of 10 mM phosphate buffer was added to the reaction vial. After gentle stirring and removal of a 1 mL aliquot to determine the starting concentration, 31.23 g of thiol-functionalized fumed silica nanoparticles were added slowly under medium mechanical stirring. Mechanical stirring was continued for two hours to effectively disperse the reaction mixture. The resulting slurry was thick and brown and very little settling was observed upon when the mechanical stirring was stopped. Next, 2,2-dimethoxy-2-phenylacetophenone (106 mg, 0.41 mmol) was added and the reaction vessel was purged with nitrogen for 15 minutes. The vial was sealed and then put in a UV-chamber (365 nm) for 24 hours. The reaction solution was stirred briefly after 2 hours, 18 hours, and 24 hours. After completion, the product was filtered and washed two times with 250 mL of phosphate buffer (pH=7), twice with 250 mL of 1.2 M $K_2CO_3$/0.8 M $KHCO_3$ solution (pH=10.2, and two times with 250 mL of 0.5M $K_2CO_3$/0.5M $KHCO_3$ solution (pH=10). The resulting product was spun down and brought to dryness via shell-freezing at −78° C., followed by lyophilization. The amount of bound protein was determined via UV-Vis spectroscopy to be 177 mg of CA/g of fumed silica. FIG. 7 shows the FTIR spectroscopic analysis of fumed silica (top) and CA-functionalized fumed silica (bottom). This was confirmed independently using thermogravimetric analysis (FIG. 8), which suggested that approximately 22% of the mass was attributed to allyl-PEG functionalized carbonic anhydrase protein.

Example 9

Figure 11:
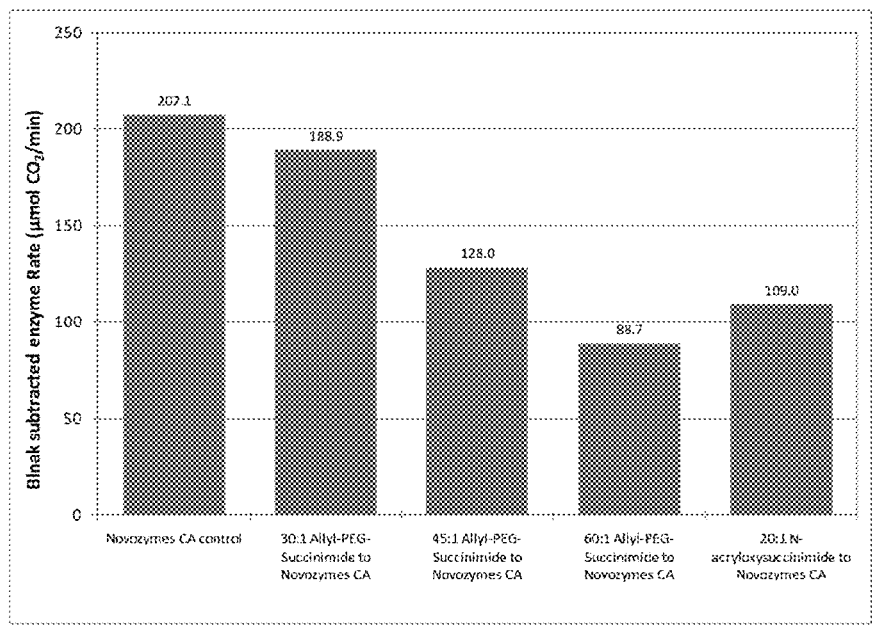
FIG. 11 is a graph of the pH stat activity comparison of various vinyl-functionalized Novozymes CA as compared to an unmodified enzyme control. The reaction conditions were as follows: 5 µg of enzyme, 1000 sccm 10% $CO_2$, 50 mL 30 mM tris(hydroxymethyl)methylamine (Tris) buffer (pH=8.6).

Enzymatic Activity of Carbonic Anhydrase Immobilized on Fumed Silica Nanoparticles Determined Using a pH Stat Assay A pH stat assay was used to determine carbonic anhydrase activity. The quantity of aqueous potassium hydroxide needed to maintain the pH of a buffered solution as $CO_2$ was sparged into was directly related to the number of $CO_2$ molecules being converted to carbonic acid by the enzyme. The instrumental setup included a water-jacketed vessel to maintain temperature, a thermometer, a pH-probe, an automated buret (Metrohm 842 Titrando), a sintered glass frit, a mass flow controller, and a stir plate with stir bar. In a typical assay, 50 mL of a 30 mM Tris buffer solution (pH 8.6) was added to a water jacketed vessel maintained at a temperature of 8° C. Enzyme was added to the solution and the pH probe, thermometer, burette, and sintered glass sparger were lowered into the enzyme-containing solution. A 10% $CO_2$ (90% $N_2$) feed gas, which was controlled at 1 standard liters per minute (SLPM) by a mass flow controller, was delivered to the solution through the sintered glass sparger. The solution was constantly stirred by a stir bar at the bottom of the vessel at a rate of 1500 rpm. As the carbonic anhydrase enzyme converted $CO_2$ into carbonic acid (which dissociates to hydronium and bicarbonate ions in water) the pH of the solution began to drop. Titration of the assay solution with aqueous potassium hydroxide was automated, and controlled by the signal of the pH probe through a negative feedback mechanism. The titration was allowed to proceed for 100 seconds, to establish a steady-state, before data was collected. After the initial 100 seconds of titration, data was logged and plotted as a rate of change in potassium hydroxide volume delivered (mL) vs. change in time (minutes). The slope of the plot in this graph represented the rate of enzyme activity. As the concentration of the potassium hydroxide solution was known and the reaction of hydroxide ion with hydronium ion has 1:1 stoichiometry, the slope of the plot could easily be converted into an enzymatic rate in units of μmol/min (FIG. 11).

Figure 12:
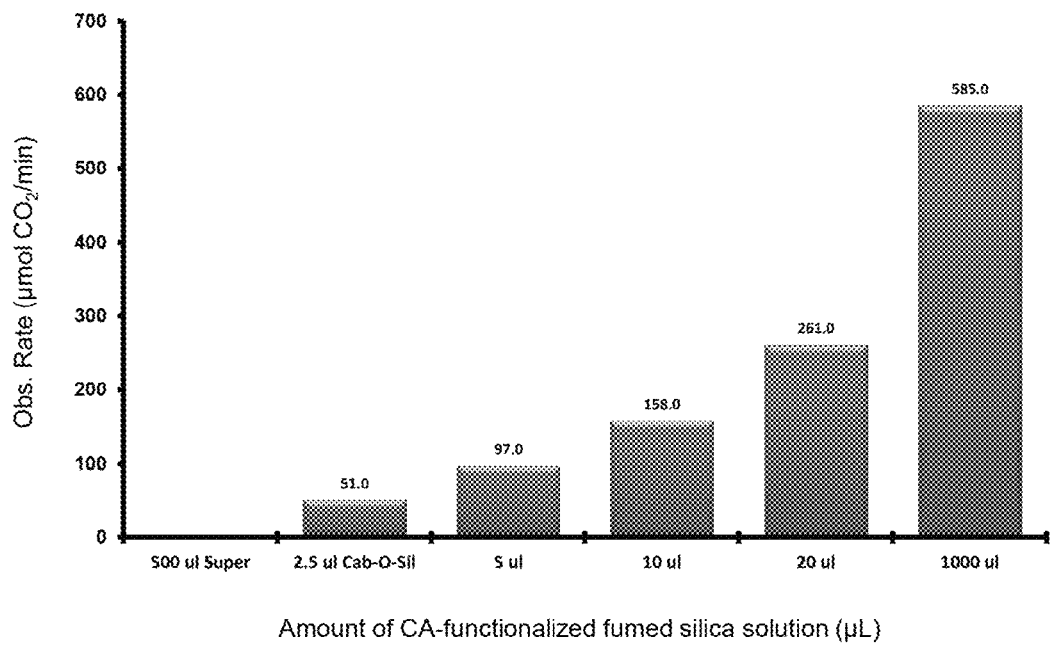
FIG. 12 is a graphical representation of the enzymatic activity of carbonic anhydrase functionalized fumed silica nanoparticles measured with a pH-stat assay.

The enzymatic activity of carbonic anhydrase immobilized on fumed silica nanoparticles (CA/fumed silica) was determined using a pH stat assay as described above. A stock solution of CA/fumed silica was prepared in 0.5 M potassium bicarbonate/0.5 M potassium bicarbonate solution (17.6 mg fumed silica/mL buffer). An aliquot of this stock solution was centrifuged and the resulting supernatant was tested via pH stat assay for activity towards catalytic conversion of $CO_2$ to carbonic acid; no measurable amount of activity was observed above the blank buffer. The CA/fumed silica solution was then diluted 10 fold (1.76 mg/mL) in 30 mM Tris buffer solution (pH 8.6), and the suspension was well dispersed using probe sonication and mechanical stirring. Different volumes of this stock solution were dosed into the pH stat, after 15 seconds of vortexing to ensure dispersion, according to the procedure described above (FIG. 12).

Example 10

Figure 13:
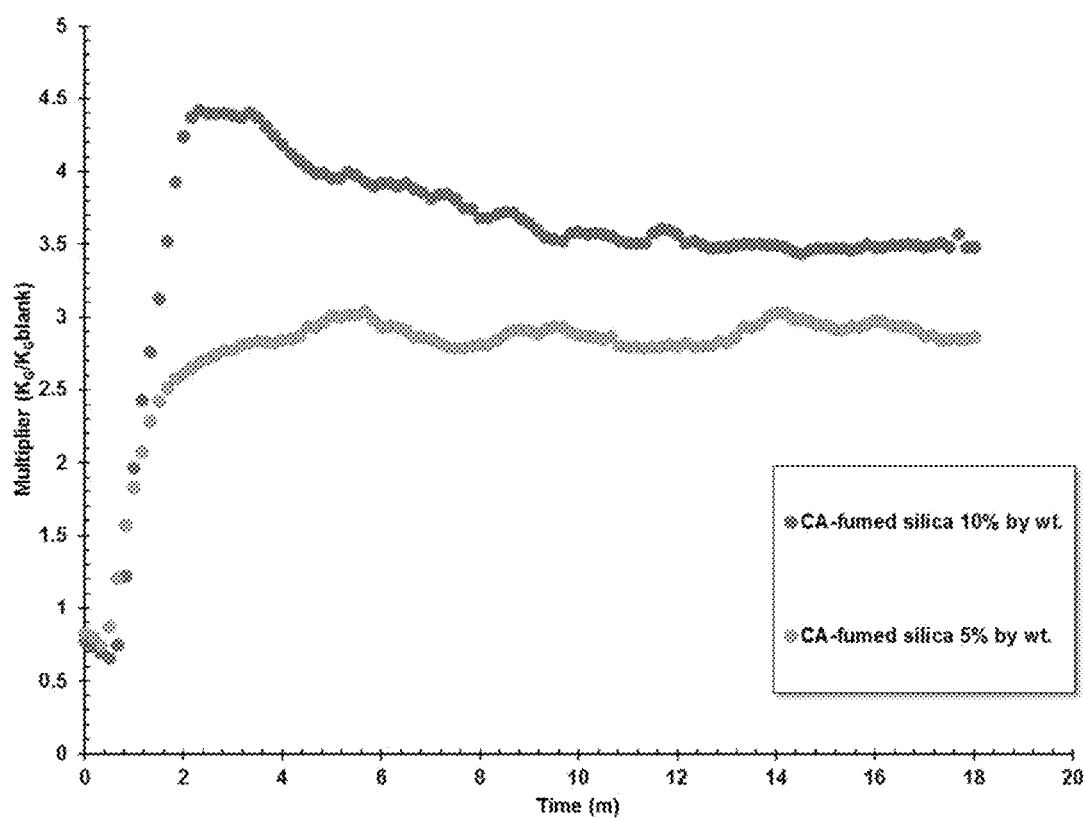
FIG. 13 is a graphical representation of the enzymatic activity of carbonic anhydrase functionalized fumed silica nanoparticles, measured in a single-pass flow-through reactor.

Enzymatic Activity of Carbonic Anhydrase Immobilized on Fumed Silica Nanoparticles Determined Using a Single-Pass Flow-Through Reactor and Packed Bed Absorber Column To determine the enzymatic activity of carbonic anhydrase immobilized on fumed silica nanoparticle (CA/fumed silica), a single-pass flow-through reactor which functioned as a small scale reactor (without a stripper to regenerate the solvent) was utilized. The packed bed absorber column was a 78.5 cm tall×⅝" i.d. counter-flow column packed with ceramic balls. The absorber solution was a well dispersed suspension of carbonic anhydrase immobilized on fumed silica nanoparticles in a 0.8 M potassium bicarbonate/1.2 M potassium carbonate solution (ca. pH=10). Carbon dioxide conversion studies were conducted using 10% and 5% by weight solutions of carbonic anhydrase/fumed silica, and were compared to blank solutions of potassium carbonate. The absorber solution was at 30° C. and was dripped at a rate of 25 ml/min from the top of the column while feed gas (15% $CO_2$, 85% $N_2$) flowed upward from the bottom of the column. To quantitate $CO_2$ conversion, a non-dispersive infrared detector (NDIR) was used to monitor the $CO_2$ gas at the output of the column, and the differential between the $CO_2$ content of the output gas versus the feed gas was used to calculate the rate of absorption. The 10% by weight solution of CA/fumed silica showed an overall mass transfer coefficient ($K_G$) of 0.094. This corresponds to 53% $CO_2$ conversion and a 4.5 fold enhancement of activity as compared to a blank absorber solution of potassium carbonate (FIG. 13). For the 5% by weight solution of CA/fumed silica, an overall mass transfer coefficient ($K_G$) of 0.062 was calculated. This corresponds to 39% $CO_2$ conversion and a 3 fold enhancement of activity as compared to a blank absorber solution of potassium carbonate (FIG. 13). Each run was tested for a duration of 18 minutes and sustained conversion over this time was observed.

Example 11

Enzymatic Activity of Carbonic Anhydrase Immobilized on Ceramic Balls Determined Using a Single-Pass Flow-Through Reactor and Packed Bed Absorber Column The enzymatic activity of carbonic anhydrase immobilized on ceramic balls (CA/ceramic balls) was tested in a single-pass flow-through reactor in a similar manner as described in Example 11. However, in these tests, the absorber solution was 0.8 M potassium bicarbonate/1.2 M potassium bicarbonate solution (ca. pH=10) and was not a suspension. The packed bed absorber column was packed with CA/ceramic balls. The duration of the testing time in these studies varied between 25 and 45 min. These experiments establish precedent and proof-of-concept that absorber packing structures can be effectively modified using thiol-ene coupling chemistries. Quantification of $CO_2$ conversion was performed as described in Example 11. Carbonic anhydrase immobilized on ceramic balls (via either photo-initiated or redox initiated thiol-ene reactions) were found to have as high as 2.0 to 2.4 fold enhancement of overall mass transfer coefficients ($K_G$) as compared to bare, unfunctionalized ceramic packing ($K_G$ blank) (Table 1). This conversion was sustained over the course of the testing and no appreciable loss in enzyme or activity was observed.

TABLE 1

Summary of enzymatic activity of CA/ceramic balls determined using a single-pass flow-through reactor.

| Enzyme | Description | Estimated CA Loading on Packing (g CA/L packing) | Time (min) | $CO_2$ % conversion | KG (mmol/s · m² · kPa) | Rate Constant Multiplier |
|---|---|---|---|---|---|---|
| Acryl-PEG CA | redox-initiated click coupling, 2 h, 30:1 acrylamide CA | 50 mg | T = 0<br>T = 30 | 21%<br>19% | 0.03<br>0.03 | 1.71<br>1.54 |
| Allyl-PEG CA | redox-initiated click coupling, 2 h, ally-PEG CA | 54 mg | T = 0<br>T = 30 | 18%<br>17% | 0.02<br>0.02 | 1.43<br>1.37 |
| Allyl-PEG CA | redox-initiated click coupling, 24 h, ally-PEG CA | 50 mg | T = 0<br>T = 30 | 26%<br>19% | 0.04<br>0.03 | 2.18<br>1.54 |
| Allyl-PEG CA | redox-initiated click coupling, 24 h, ally-PEG CA | NA | T = 0<br>T = 30 | 24%<br>21% | 0.04<br>0.03 | 2.00<br>1.69 |
| Allyl-PEG CA | photo-initiated click coupling, 24 h, ally-PEG CA | NA | T = 10<br>T = 20 | 32%<br>27% | 0.05<br>0.05 | 2.40<br>1.90 |

A single pass reactor test using the single pass reactor depicted in FIG. 1 was designed to measure an overall mass transfer coefficient relative to a known packing surface area, $K_{G,P}$. The ratio of $K_{G,P}$ measurements for immobilized enzyme coated packing samples and bare (un-coated) gives a multiplier in overall mass transfer coefficient:

Multiplier: $X_{KG} = K_{G,P}(\text{enzyme})/K_{G,P}(\text{blank})$.

A bottle of a dry test gas mixture (1) is used to supply a known feed gas composition (e.g., 15 vol % $CO_2$ in nitrogen) at a flow of 400 SCCM through a calibrated mass flow controller (2) into an inlet tee (3) positioned below a 15.88 mm ID packed column reactor (4). The packed column (4) contains a known mass of model packing (e.g., Tipton ceramic spheres, ~0.366 cm diameter and 7.158 cm2/g, and ~47.5% void fraction) such that the total packing surface area in the reactor is known. The feed gas containing $CO_2$ flows upward through the packed column (4) and becomes partially depleted in $CO_2$ as a certain amount is transferred into the down-flowing absorbent liquid. The treated gas exits the reactor at (5) and then passes through a back pressure regulator (6) that maintains a constant back pressure of approximately 0.07 bar, or 1.07 bar total pressure. A smaller slip stream of treated gas is collected before the back pressure valve (6) and flows at ~60 mL/min using a flow indicating manual control valve (7) that feeds a drying column (8) (~0.5 cm ID tube containing Dryerite granules) before delivery to a calibrated continuous gas analyzer (9), a non-dispersive infrared analyzer by Quantek (0% to 20% $CO_2$ range with 0.01% resolution and stated precision of <2% of reading and not less than ±0.2% absolute scale for its maximum accuracy).

A supply of absorbent solution (10) is prepared with potassium carbonate and bicarbonate to simulate a known $CO_2$ pre-loading, sometimes referred to as the fractional conversion of carbonate to bicarbonate, $X_C$. Approximately 1 liter of 20 wt % $K_2CO_3$ equivalent with $X_C$=25% converted to bicarbonate is prepared by mixing 175.22 g $K_2CO_3$ (<99.9% pure), 84.62 g $KHCO_3$ (>99.9% pure), and 926.91 g water (purified). This mixture has a pH of ~10.08 to 10.1 at 22 to 23° C. corresponding to HCO3-/CO3=molar ratio of 0.667, and XC/(1−XC)=33.3%. The lean absorbent solution is metered at 25 mL/min using a peristaltic pump (11), and flow is checked with a flow indicator (12) before delivery to the packed column reactor (4). The rich liquid exits the reactor at (13) and passes into the waste reservoir (14) through a liquid seal as shown in the figure. A vent line (15) is added to maintain pressure balance between the supply reservoir and the waste receiver reservoir.

The packed column typically employs approximately 65 grams of uncoated (bare) model ceramic spheres (e.g., Tipton Spheres, ~0.366 cm diameter and 7.158 cm2/g), or the equivalent mass of bare packing that was subsequently coated with immobilized enzyme. The dry void fraction of bare random packing is ~47.5%, and liquid hold up is approximately 15%, and the coated packing is assumed to have the approximately the same void fraction as the bare. The height of the packed column (4) for immobilized enzyme compared to the height of the same amount of bare packing is used to estimate the average film thickness of the immobilized enzyme coating and thus make a correction to the gross surface area in the column after coating.

Calculations: The $CO_2$ capture, $X_{CO2}$ (also referred to as the $CO_2$ conversion), is calculated from the relative flow of $CO_2$ from inlet to exit, and therefore can be related to the dry $CO_2$ mole fractions at points (2) and (5) as follows:

$$X_{CO2} \equiv 1 - \frac{(F_{CO2})_{out}}{(F_{CO2})_{in}} = 1 - \frac{F_{T,(5)}(y_{CO2,(5)})}{F_{T,(2)}(y_{CO2,(2)})} = \frac{y_{CO2,(2)} - y_{CO2,(5)}}{y_{CO2,(2)}(1 - y_{CO2,(5)})}$$

Where $F_{CO2,out}$ and $F_{CO2,in}$ are the mole flows of $CO_2$ at the outlet and inlet of reactor (4) respectively; likewise, FT,(5) and FT,(2) are the total dry gas equivalent mole flows at points (5) and (2) respectively, with $y_{CO2,(5)}$ and $y_{CO2,(2)}$ representing the dry basis $CO_2$ mole fractions quantified for the noted process points.

The following is an integrated form of the design equation for an isothermal plug flow reactor undergoing a first order reversible reaction—assuming constant equilibrium $CO_2$ partial pressure by test design ($X^*_{CO2}$ is a function of $P^*_{CO2}$, and thus constant for the test conditions) and also a dilute gas assumption is made for convenience:

$$\ln\left(\frac{X^*_{CO2} - X_{CO2}}{X^*_{CO2}}\right) = k_1 t_g$$

The first order rate constant, $k_1$, can be related to the overall mass transfer coefficient, $K_G$, while $t_g$ represents the gas phase residence time. The equilibrium $CO_2$ capture, $X^*$, is calculated based on the known equilibrium $CO_2$ partial pressure at the average $CO_2$ loading—the liquid to gas ratio is set to be high, e.g., ~60:1 (mass basis), so that change in $CO_2$ loading across the reactor will be relatively slight. The overall mass transfer coefficient relative to the packing area, $K_{GP}$, is related to $k_1$ as follows:

$$K_{G,P} = \frac{k_1}{a_p RT}$$

The gas residence time is calculated from the total packing volume relative to the volumetric flow rate, corrected for void fraction and liquid hold up:

$$t_g = \frac{V}{v_o}(\phi_v - \phi_1)$$

The overall mass transfer coefficients reported here, are based on the packing area, $K_{G,P}$, not gas-liquid interfacial area, for which we use the alternative notation $K_{G,I}$ for clarity. The $K_{G,I}$ are well known from measurements in idealized laminar film reactors (e.g., wetted wall column) for several $CO_2$ active sorbent solutions. Literature reported $K_{G,I}$ can be compared to $K_{G,P}$ measurements reported herein if including an area effectiveness, $\eta_a$:

$$K_{G,I} = \frac{K_{G,P}}{\eta_a}$$

The area effectiveness can be determined by comparison of blank tests in the packed column with wetted wall column measurements using potassium carbonate under equivalent conditions. The test conditions reported here are estimated to have an area effectiveness of $\eta_a$=~29 to 30%.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there can be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. An immobilized biocatalyst comprising
a substrate; and
a biocatalyst linked to the substrate through a linking moiety comprising a $C_1$ to $C_{30}$ alkylene wherein at least one of the —$CH_2$— groups of the alkylene group is replaced by —S—; and optionally, each of one or more of the other —$CH_2$— groups of the alkylene group is independently replaced by —($CH_2$—$CH_2$—O)$_x$—, —O—, —C(O)—, —$NR_3$—, —Si($OR_1$)($OR_2$)—, —Si($R_5$)($OR_2$)—, —Si(Cl)(Cl)—, arylene, cycloalkylene, heteroarylene, or heterocyclo; or optionally, each of one or more of the other —$CH_2$— groups of the alkylene group is independently substituted with a —OH, —$NR_3R_4$, or —C(O)OH, wherein x is an integer from 4 to 2300, $R_1$ and $R_2$ are independently hydrogen, alkyl, or another silicon atom attached to the substrate through an —O— group, $R_3$ and $R_4$ are independently hydrogen, alkyl, or —CHO, and $R_5$ is alkyl;
wherein the biocatalyst catalyzes hydration of carbon dioxide.

2. The immobilized biocatalyst of claim 1 wherein the linking moiety comprises a $C_1$ to $C_{20}$ alkylene wherein at least one of the —$CH_2$— groups of the alkylene group is replaced by —S—, and optionally, each of one or more of the other —$CH_2$— groups of the alkylene group is independently replaced by —($CH_2$—$CH_2$—O)$_x$—, —O—, —C(O)—, —$NR_3$—, or —Si($OR_1$)($OR_2$)—, and each of one or more of the other —$CH_2$— groups of the alkylene group is independently substituted with a —OH, or —C(O)OH, wherein x is an integer from 4 to 2300, $R_1$ and $R_2$ are independently hydrogen, methyl, or another silicon atom attached to the substrate through an —O— group, and $R_3$ is hydrogen.

3. The immobilized biocatalyst of claim 1 wherein the linking moiety comprises a $C_1$ to $C_{20}$ alkylene wherein at least one of the —$CH_2$— groups of the alkylene group is replaced by —S—, and each of one or more of the other —$CH_2$— groups of the alkylene group is independently replaced by —($CH_2$—$CH_2$—O)$_x$—, —O—, —C(O)—, —$NR_3$—, or —Si($OR_1$)($OR_2$)—, and each of one or more of the other —$CH_2$— groups of the alkylene group is independently substituted with a —C(O)OH, wherein x is an integer from 4 to 2300, $R_1$ and $R_2$ are independently hydrogen, methyl, or another silicon atom attached to the substrate through an —O— group, and $R_3$ is hydrogen.

4. The immobilized biocatalyst of claim 1 wherein the substrate comprises a solid support.

5. The immobilized biocatalyst of claim 4 wherein the substrate is a ceramic, a silicate, alumina, stainless steel, titania, or a combination thereof.

6. The immobilized biocatalyst of claim 5 wherein the substrate comprises microparticles.

7. The immobilized biocatalyst of claim 6 wherein the biocatalyst comprises carbonic anhydrase.

8. The immobilized biocatalyst of claim 5 wherein the substrate comprises nanoparticles.

9. The immobilized biocatalyst of claim 8 wherein the biocatalyst comprises carbonic anhydrase.

10. The immobilized biocatalyst of claim 1 wherein the biocatalyst comprises carbonic anhydrase.

11. The immobilized biocatalyst of claim 10 wherein the carbonic anhydrase comprises a cytosolic carbonic anhydrase, a mitochondrial carbonic anhydrase, a secreted carbonic anhydrase, or a membrane-associated carbonic anhydrase.

12. The immobilized biocatalyst of claim 11 wherein the carbonic anhydrase comprises a mammalian carbonic anhydrase, a plant carbonic anhydrase, or a microbial carbonic anhydrase.

13. The immobilized biocatalyst of claim 2 wherein the biocatalyst comprises carbonic anhydrase.

14. The immobilized biocatalyst of claim 3 wherein the biocatalyst comprises carbonic anhydrase.

15. A system for removing $CO_2$ from a $CO_2$-containing gas comprising a reaction vessel comprising a bottom portion containing a gas inlet and a liquid outlet, a top portion containing a liquid inlet and a gas outlet, and a middle portion containing a plurality of the immobilized biocatalysts of claim 10, the biocatalyst or enzyme being carbonic anhydrase and the carbonic anhydrase being capable of catalyzing hydration of $CO_2$ into hydrogen ions and bicarbonate ions.

16. The system of claim 15 wherein the substrate comprises microparticles.

17. The system of claim 15 wherein the substrate comprises nanoparticles.

18. A process for removing $CO_2$ from a $CO_2$-containing gas, the process comprising
contacting a gas comprising $CO_2$ with a water-containing liquid and an immobilized biocatalyst of claim 10 to catalyze hydration of the $CO_2$ with water and form hydrogen ions and bicarbonate ions.

19. The process of claim 18 wherein the water-containing liquid is an aqueous solution.

20. The process of claim 19 wherein the substrate comprises microparticles.

21. The process of claim 19 wherein the substrate comprises nanoparticles.

* * * * *